(12) United States Patent
McDonnell et al.

(10) Patent No.: US 7,307,102 B2
(45) Date of Patent: Dec. 11, 2007

(54) METHOD OF PREVENTING OR TREATING ESTROGEN-DEPENDENT DISEASES AND DISORDERS

(75) Inventors: Donald P. McDonnell, Chapel Hill, NC (US); John Norris, Raleigh, NC (US); Caroline Connor, Durham, NC (US); Ashini Wijayaratne, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 10/390,032

(22) Filed: Mar. 18, 2003

(65) Prior Publication Data

US 2003/0232795 A1 Dec. 18, 2003

Related U.S. Application Data

(63) Continuation of application No. 09/134,146, filed on Aug. 14, 1998, now abandoned.

(60) Provisional application No. 60/055,881, filed on Aug. 15, 1997.

(51) Int. Cl.
*A61K 31/235* (2006.01)
(52) U.S. Cl. .................................... 514/532
(58) Field of Classification Search ................ 514/364, 514/520, 532, 570, 617
See application file for complete search history.

(56) References Cited

U.S. PATENT DOCUMENTS

| | | | |
|---|---|---|---|
| 3,341,537 A | 9/1967 | Richardson et al. | 260/247.2 |
| 3,493,606 A | 2/1970 | Richardson | 260/501.18 |
| 3,637,856 A | 1/1972 | Landquist et al. | 260/570 |
| 4,198,435 A | 4/1980 | Richardson | 424/330 |
| 4,206,234 A | 6/1980 | Richardson | 424/330 |
| 4,307,111 A | 12/1981 | Crawley | 424/278 |
| 4,536,516 A | 8/1985 | Harper et al. | 514/514 |
| 4,623,660 A | 11/1986 | Richardson | 514/514 |
| 4,760,053 A | 7/1988 | Labrie | 514/18 |
| 4,803,227 A | 2/1989 | Brandes et al. | 514/651 |
| 4,851,433 A | 7/1989 | Kraus | 514/648 |
| 4,859,695 A | 8/1989 | McKissick et al. | 514/408 |
| 4,894,373 A | 1/1990 | Young | 514/239.2 |
| 4,960,937 A | 10/1990 | Woschina et al. | 564/324 |
| 5,047,431 A | 9/1991 | Schickaneder et al. | 514/648 |
| 5,119,827 A | 6/1992 | Osborne et al. | 128/749 |
| 5,189,212 A | 2/1993 | Ruenitz | 562/468 |
| 5,393,785 A | 2/1995 | Labrie et al. | 514/622 |
| 5,410,080 A | 4/1995 | Bitonti et al. | 564/323 |
| 5,455,275 A | 10/1995 | Fontana | 514/648 |
| 5,491,173 A | 2/1996 | Toivola et al. | 514/648 |
| 5,550,164 A | 8/1996 | Fontana | 514/648 |
| 5,681,835 A | 10/1997 | Willson | 514/237.5 |
| 5,877,219 A | 3/1999 | Wilson | 514/617 |
| 6,207,716 B1 | 3/2001 | Willson | 514/617 |

FOREIGN PATENT DOCUMENTS

| | | |
|---|---|---|
| EP | 0 054 168 | 6/1982 |
| EP | 0 095 875 | 12/1983 |
| EP | 0 178 862 | 4/1986 |
| EP | 0 272 330 | 6/1988 |
| EP | 0 589 039 A1 | 3/1994 |
| GB | 1029221 | 5/1966 |
| GB | 1064629 | 4/1967 |
| GB | 1079747 | 8/1967 |
| GB | 2 058 061 | 4/1981 |
| WO | WO 92/04310 | 3/1992 |
| WO | WO 92/06068 | 4/1992 |
| WO | WO 92/19585 | 11/1992 |
| WO | WO 94/23708 | 10/1994 |

OTHER PUBLICATIONS

Wilson, T. M. et al "A non-steroidal estrogen with functional selectivity for bone over uterus in rats" J. Med. Chem. (1994) vol. 3 pp. 1550-1552.*
Willson, T. M., et al; "Dissection of the Molecular Mechanism of Action of GW5638, a Novel Estrogen Receptor Ligand, Provides Insights into the Role of Estrogen Receptor in Bone"; *Endocrinology*; vol. 138, No. 9; pp. 3901-3911 (1997).
Shao, W., et al.; Coactivator AIB1 links estrogen receptor transcriptional activity and stability; *PNAS*; vol. 101, No. 32; pp. 11599-11604 (2004).
van Duijn, Menopause and the brain, J Psychosom Obstet Gynaecol. Jun. 1997;18(2):121-5 (Abstract).
Schneider et al, Can estrogens prevent neurodegeneration?, Drugs Aging. Aug. 1997;11(2):87-95 (Abstract).
Klein et al, Are sex hormones associated with age-related maculopathy in women? The Beaver Dam Eye Study. Trans Am Ophthalmol Soc. 1994;92:289-95; discussion 295-7 (Abstract).
Smith et al, Gender, oestrogen, hormone replacement and age-related macular degeneration: results from the Blue Mountains Eye Study. Aust N Z J Opthalmol. May 1997;25 Suppl 1:S13-5 (Abstract).
Fantl et al, Estrogen therapy in the management of urinary incontinence in postmenopausal women: a meta-analysis. First rept of the Hormones and Urogenital Ther. Com., Obstet Gynecol. Jan. 1994;83(1):12-8 (Abstract).
Elia et al, Estrogen effects on the urethra: beneficial effects in women with genuine stress incontinence, Obstet Gynecol Surv. Jul. 1993;48(7):507-17 (Abstract).
Ferrara et al, Sex differences in insulin levels in older adults and the effect of body size, estrogen replacement therapy, and glucose tolerance status. The Rancho Bernardo Study, 1984-1987, Diabetes Care, Feb. 1995;18(2):220-5 (Abstract).
Song et al, Molecular characterization of a testis-specific estrogen sulfotransferase and aberrant liver expression in obese and diabetogenic C57BL/KsJ-db/db mice, Endocrinology. Jun. 1995; 136(6):2477-84 (Abstract).

(Continued)

*Primary Examiner*—Leigh C. Maier
(74) *Attorney, Agent, or Firm*—Nixon & Vanderhye P.C.

(57) ABSTRACT

The present invention relates, in general, to the treatment of estrogen-dependent diseases and disorders and, in particular, to a method of treating estrogen-dependent cancers, particularly breast cancer, with antiestrogens.

8 Claims, 19 Drawing Sheets

OTHER PUBLICATIONS

Bracken et al, Conception delay after oral contracep. use: the effect of estrogen dose, Fertil Steril. Jan. 1990;53(1):21-7 (Abstract).

Jequier, Conception in the resistant ovary syndrome occurring during hormone replacement therapy: a report of 2 cases, Aust N Z J Obstet Gynaecol. May 1990;30(2):176-8 (Abstract).

Pavlik et al, "Resistance to Tamoxifen with Persisting Sensitivity to Estrogen: Possible Mediation by Excessive Antiestrogen Binding Site Activity", Cancer Research 52:4106-4112 (1992).

Nicolaus, "Symbiotic Approach to Drug Design" Decision Making in Drug Research, edited by Franz Gross, Raven Press, New York, pp. 173-186 (1983).

Hartmann et al, "Antiestrogen resistance in ER positive breast cancer cells", Breast Cancer Res. Treat. 31(2-3):301-307 (1994)—Abstract.

deGraffenried et al, "Regulation of the estrogen receptor alpha minimal promoter by Spl, USF-1 and ERalpha", Breast Cancer Res. Treat. 85(2):111-120 (2004) abstract.

Willson et al, "3-[4-(1,2-Diphenylbut-1-enyl)phenyl]acrylic Acid: A Non-Steriodal Estrogen with Functional Selectivity for Bone over Uterus in Rats", J. Med. Chem. 37:1550-1552 (1994).

Howell et al, "Response to a specific antioestrogen (ICI 182780) in tamoxifen-resistant breast cancer", The Lancet 345:29-30 (1995).

Buzdar et al, "Phase II Evaluation of Ly156758 in Metastatic Breast Cancer", Oncology 45:344-345 (1988).

Tzukerman et al, "Human Estrogen Receptor Transactivational Capacity Is Determined by both Cellular and Promoter Context and Mediated by Two Functionally Distinct Intramolecular Regions", Molecular Endocrinology 8(1):21-30 (1994).

McDonnell and Norris, "Analysis of the Molecular Pharmacology of Estrogen Receptor Agonists and Antagonists Provides Insights into the Mechanism of Action of Estrogen in Bone", Osteoporosis Int. Suppl. 1:S0-S00 (1997).

McDonnell et al, "Analysis of Estrogen Receptor Function in Vitro Reveals Three Distinct Classes of Antiestrogens", Molecular Endocrinology 9(6):659-669 (1995).

Jordan and Murphy, "Endocrine Pharmacology of Antiestrogens as Antitumor Agents", Endocrine Reviews 11(4):578-610 (1990).

Lerner and Jordan, "Development of Antiestrogens and Their Use in Breast Cancer: Eighth Cain Memorial Award Lecture", Cancer Research 50:4177-4189 (1990).

Jordan et al, "Structural Requirements for the Pharmacological Activity of Nonsteroidal Antiestrogens in Vitro", Molecular Pharmacology 26:272-278 (1984).

Jordan et al, "A monohydroxylated Metabolite of Tamoxifen with Potent Antioestrogenic Activity", J. Endocr. 75:305-316 (1977).

Jordan and Gosden, Importance of the Alkylaminoethoxy Side-Chain For The Estrogenic and Antiestrogenic Actions of Tamoxifen and Trioxifene in the Immature Rat Uterus Moleculear and Cellular Endocrinology 27:291-306 (1982).

Jarman et al, "Analogues of tamoxifen: the role of the basic side-chain. Applications of a whole-cell oestrogen-receptor binding assay to N-oxides and quaternary salts", Anti-Cancer Drug Design 1:259-268 (1986).

Murphy and Jordan, "Structural Components Necessary For The Antiestrogenic Activity Of Tamoxifen", J. Steroid Biochem. 34(1-6):407-411 (1989).

Harper and Walpole, "Contrasting Endocrine Activities of *cis* and *trans* Isomers in a Series of Substituted Triphenylethylenes", Nature 5057:87 (1966).

Jordan et al, "Geometric Isomers of Substituted Triphenylethylenes and Antiestrogen Action", Endocrinology 108(4):1353-1361 (1981).

Katzenellenbogen et al, "Bioactivities, Estrogen Receptor Interactions, and Plasminogen Activator-inducing Activities of Tamoxifen and Hydroxy-tamoxifen Isomers in MCF-7 Human Breast Cells", Cancer Research 44:112-119 (1984).

Katzenellenbogen et al, "Facile Geometric Isomerization of Phenolic Non-Steroidal Estrogens and Antiestrogens: Limitations To The Interpretation Of Experiments Characterizing The Activity Of Individual Isomers", J. Steroid Biochem. 22(5):589-596 (1985).

McCague et al, "Synthesis and Estrogen Receptor Binding of 6,7-Dihydro-8-phenyl-9-[4-[2-(dimethylamino)ethoxy]phenyl]-5H-benzocycloheptene, a Nonisomerizable Analogue of Tamoxifen. X-ray Crystallographic Studies", J. Med. Chem. 29:2053-2059 (1986).

McCague et al, "Nonisomerizable Analogues of (Z)- and (E)-4-Hydroxytamoxifen. Synthesis and Endocrinological Properties of Substituted Diphenylbenzocycloheptenes", J. Med. Chem. 31:1285-1290 (1988).

McCague et al, "Non-Isomerisable Antiestrogens Related to Tamoxifen", J. Steroid Biochem. 31(4B):545-547 (1988).

Katzenellenbogen et al, "Efficient and Highly Selective Covalent Labeling of the Estrogen Receptor with [$^3$H]Tamoxifen Aziridine", The Journal of Biological Chemistry 258(6):3487-3495 (1983).

Harlow et al, "Identification of Cysteine 530 as the Covalent Attachment Site of an Affinity-labeling Estrogen (Ketononestrol Aziridine) and Antiestrogen (Tamoxifen Aziridine) in the Human Estrogen Receptor", The Journal of Biological Chemistry 264(29):17476-17485 (1989).

Lees et al, "Identification of two transactivation domains in the mouse oestrogen receptor", 17(14):5477-5488 (1989).

Fawell et al, "Inhibition of estrogen receptor-DNA binding by the "pure" antiestrogen ICI 164,384 appears to be mediated by impaired receptor dimerization", Proc. Natl. Acad. Sci. USA 87:6883-6887 (1990).

Love et al, "Bone mineral density in women with breast cancer treated with adjuvant tamoxifen for at least two years", Breast Cancer Research and Treatment 12:297-301 (1988).

Turken et al, "Effects of Tamoxifen on Spinal Bone Density in Women With Breast Cancer", Journal of the National Cancer Institute 81(14):1086-1088 (1989).

Fentiman et al, "Bone mineral content of women receiving tamoxifen for mastalgia", Br. J. Cancer 60:262-264 (1989).

Fornander et al, "Long-Term Adjuvant Tamoxifen in Early Breast Cancer: Effect on Bone Mineral Density in Postmenopausal Women", Journal of Clinical Oncology 8(6):1019-1024 (1990).

Rossner and Wallgren, "Serum Lipoproteins and Proteins after Breast Cancer Surgery and Effects of Tamoxifen", Atherosclerosis 52:339-346 (1984).

Bruning et al, "Tamoxifen, serum lipoproteins and cardiovascular risks", Br. J. Cancer 58:497-499 (1988).

Bertelli et al, "Adjuvant tamoxifen in primary breast cancer: influence on plasma lipids and antithrombin III levels", Breast Cancer Research and Treatment 12:307-310 (1988).

Caleffi et al, "Effect of tamoxifen on oestrogen binding, lipid and lipoprotein concentrations and blood clotting parameters in premenopausal women with breast pain", J. Endocr. 119:335-339 (1988).

Bagdade et al, "Effects of Tamoxifen Treatment on Plasma Lipids and Lipoprotein Lipid Composition", Journal of Clinical Endocrinology and Metabolism 70(4):1132-1135 (1990).

Love et al, "Effects of Tamoxifen Therapy on Lipid and Lipoprotein Levels, in Postmenopausal Patients With Node-Negative Breast Cancer", Journal of National Cancer Institute 82(16):1327-1332 (1990).

McCague et al, "Derivatives of Tamoxifen. Dependence of Antiestrogenicity on the 4-Substituent", J. Med. Chem. 32:2527-2533 (1989).

Daux and Griffin, "Structural Features Which Distinguish Estrogen Agonists And Antagonists", J. Steroid Biochem. 27(1-3):271-280 (1987).

Robertson et al, "Antiestrogen Basicity-Activity Relationships: A Comparison of the Estrogen Receptor Binding and Antiuterotrophic Potencies of Several Analogues of (z)-1,2-Diphenyl-1-[4-[2-(dimethylamino)ethoxy]phenyl]-1-butene (Tamoxifen, Nolvadex) Having Altered Basicity", J. Med. Chem. 25:167-171 (1982).

\* cited by examiner

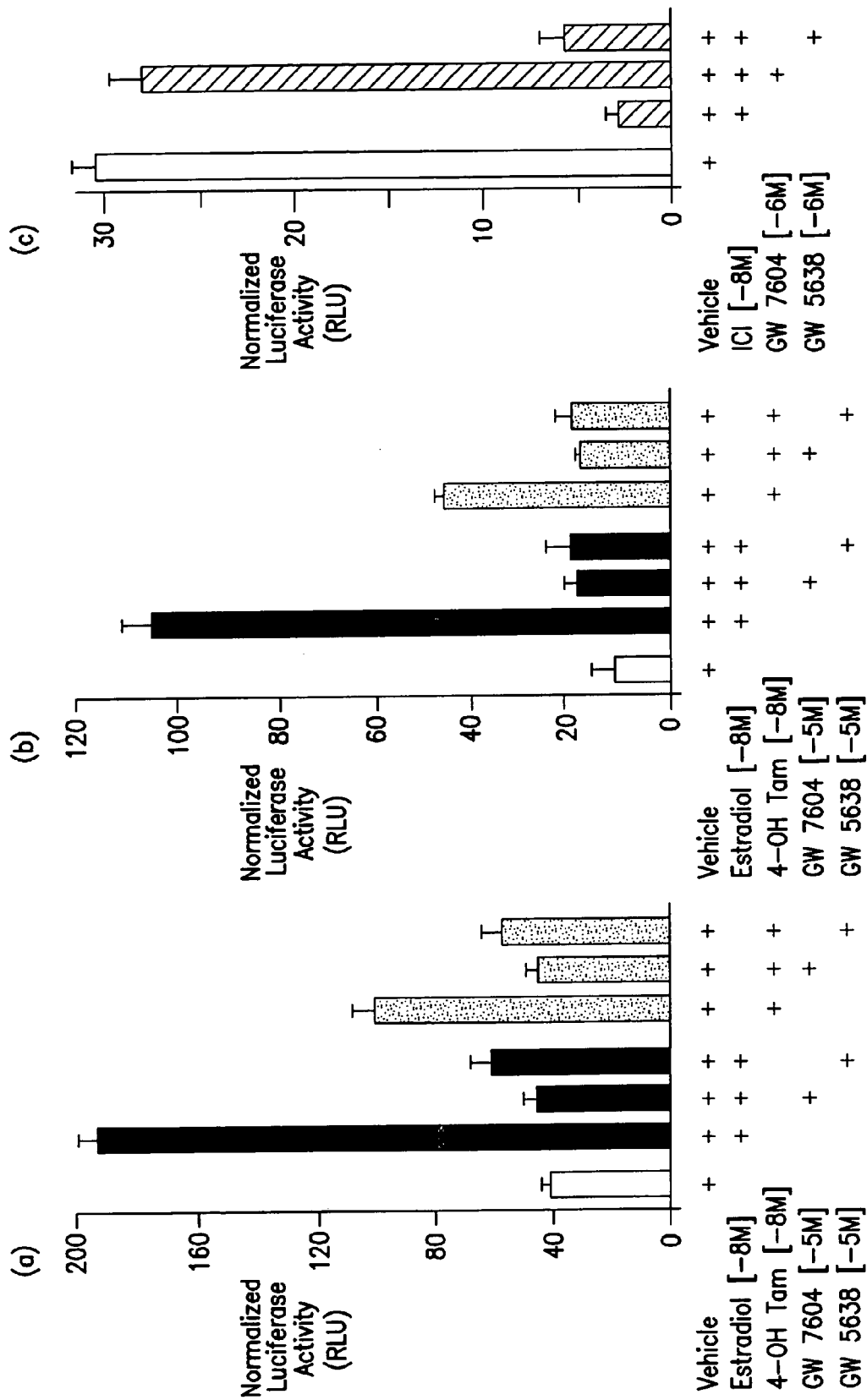

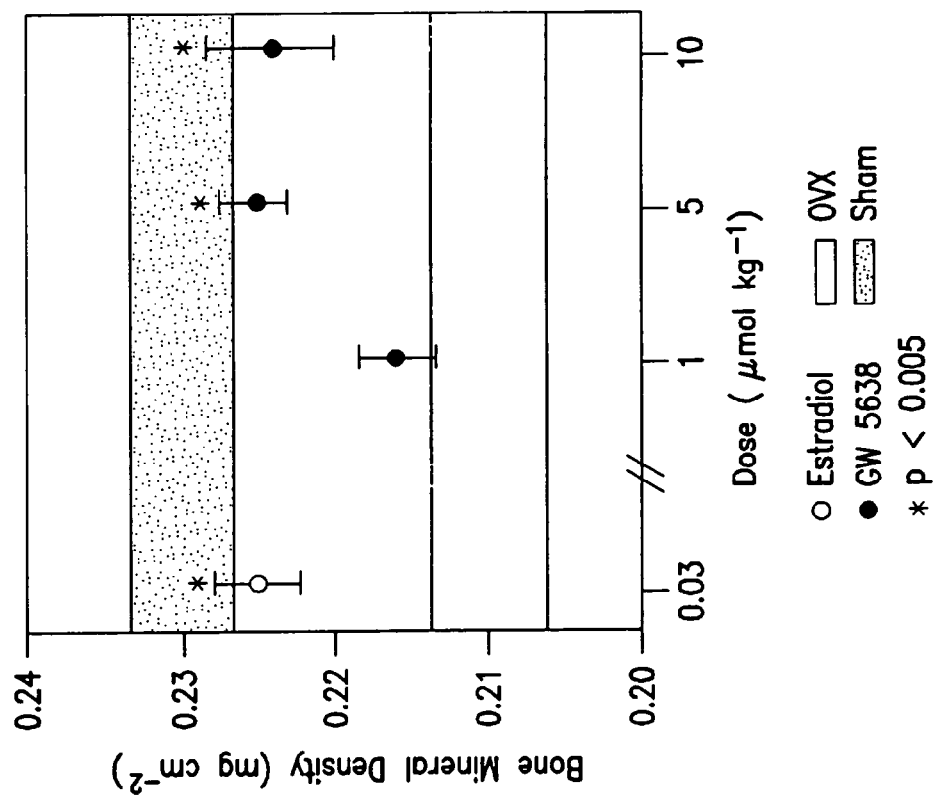
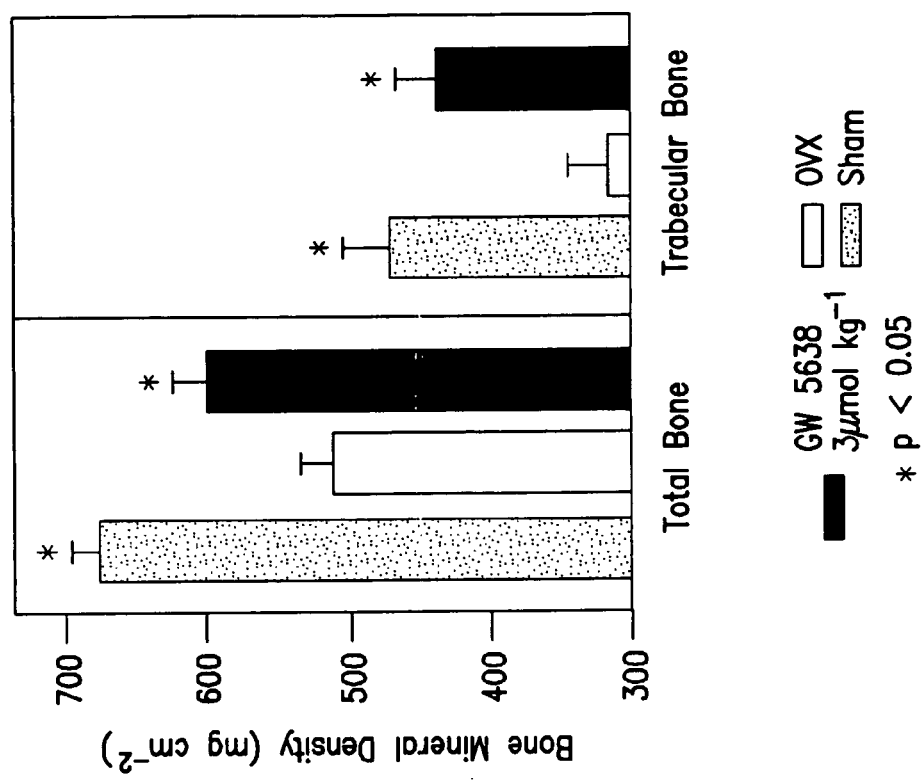
FIG. 3B
FIG. 3A

MCF-7 cells
endogenous ER protein levels

Ishikawa cells
endogenous ER protein levels

Ishikawa cells
exogenous ER protein levels

METHOD OF PREVENTING OR TREATING ESTROGEN-DEPENDENT DISEASES AND DISORDERS

This application is a continuation of Application No. 09/134,146, filed Aug. 14, 1998, now abandoned, which claims priority from Provisional Application No. 60/055,881, filed Aug. 15, 1997 the entire contents of that application being incorporated herein by reference.

This invention was made, in part, with funding from National Institutes of Health Grant No. NCI 250 CA68438. The Government may have certain rights in the invention.

TECHNICAL FIELD

The present invention relates, in general, to the treatment of estrogen-dependent diseases and disorders and, in particular, to a method of treating estrogen-dependent cancers, particularly breast cancer, with antiestrogens.

BACKGROUND

The human estrogen receptor (ER) is a member of the nuclear receptor superfamily of transcription factors (Evans, Science 240:889-895 (1988)). In the absence of hormone, it resides in the nucleus of target cells in a transcriptionally inactive state. Upon binding ligand, ER undergoes a conformational change initiating a cascade of events leading ultimately to its association with specific regulatory regions within target genes (O'Malley et al, Hormone Research 47:1-26 (1991)). The ensuing effect on transcription is influenced by the cell and promoter context of the DNA-bound receptor (Tora et al, Cell 59:477-487 (1989) (Tasset et al, Cell 62:1177-1187 (1990); McDonnell et al, Mol. Endocrinol. 9:659-669 (1995); Tzukerman et al, Mol. Endocrinol. 8:21-30 (1994)). It is in this manner that the physiological ER-agonist, estradiol, exerts its biological activity in the reproductive, skeletal and cardiovascular systems (Clark and Peck, Female Sex Steroids:Receptors and Functions (eds) Monographs on Endocrinology, Springer-Verlag, New York (1979); Chow et al, J. Clin. Invest. 89:74-78 (1992); Eaker et al, Circulation 88:1999-2009 (1993)).

In addition to these activities, estrogen has been shown to function as a mitogen in most ER-positive breast cancer cells. Thus, treatment regimens which include antiestrogens, synthetic compounds which oppose the actions of estrogen, have been effective clinically in halting or delaying the progression of the disease (Jordan and Murphy, Endocrine Reviews 11:578-610 (1990); Parker, Breast Cancer Res. Treat. 26:131-137 (1993)). The availability of these synthetic ER-modulators and subsequent dissection of their mechanism(s) of action have provided useful insights into ER action.

One of the most studied compounds in this regard is tamoxifen (Jordan and Murphy, Endocrine Reviews 11:578-610 (1990)). This compound functions as an antagonist in most ER-positive breast tumors, but displays a paradoxical agonist activity in bone and the cardiovascular system and partial agonist activity in the uterus (Kedar et al, Lancet 343:1318-1321 (1994); Love et al, New Engl. J. Med. 326:852-856 (1992); Love et al, Ann. Intern. Med. 115:860-864 (1991)). Thus, the agonist/antagonist activity of the ER-tamoxifen complex is influenced by cell context. This important observation is in apparent contradiction to long-standing models that hold that ER only exists in the cell in an active or an inactive state (Clark and Peck, Female Sex Steroids:Receptors and Functions (eds) Monographs on Endocrinology, Springer-Verlag, New York (1979)). It indicates instead that different ligands acting through the same receptor can manifest different biologies in different cells. Definition of the mechanism of this selectivity is likely to advance the understanding of processes such as tamoxifen resistance, observed in most ER-containing breast cancers, where abnormalities in ER-signaling are implicated (Tonetti and Jordan, Anti-Cancer Drugs 6:498-507 (1995)).

Using an in vitro approach, the likely mechanism for the cell selective agonist/antagonist activity of tamoxifen has been determined (Tora et al, Cell 59:477-487 (1989); Tasset et al, Cell 62:1177-1187 (1990); McDonnell et al, Mol. Endocrinol. 9:659-669 (1995); Tzukerman et al, Mol. Endocrinol. 8:21-30 (1994)). Importantly, it has been shown that tamoxifen induces a conformational change within ER which is distinct from that induced by estradiol (McDonnell et al, Mol. Endocrinol. 9:659-669 (1995); (Beekman et al, Molecular Endocrinology 7:1266-1274 (1993)). Furthermore, determination of the sequences within ER required for transcriptional activity indicate how these specific ligand-receptor complexes are differentially recognized by the cellular transcriptional machinery. Specifically, it has been shown that ER contains two activation domains, AF-1 (Activation Function-1) and AF-2, which permit its interaction with the transcription apparatus. The relative contribution of these AFs to overall ER efficacy differs from cell to cell (Tora et al, Cell 59:477-487 (1989); McDonnell et al, Mol. Endocrinol. 9:659-669 (1995); Tzukerman et al, Mol. Endocrinol. 8:21-30 (1994)). Estradiol was determined to function as both an AF-1 and an AF-2 agonist, in that it exhibited maximal activity regardless of which AF was dominant in a given cellular environment. Tamoxifen, on the other hand, functions as an AF-2 antagonist, inhibiting ER activity in cells where AF-2 is required or is the dominant activator (Tora et al, Cell 59:477-487 (1989); McDonnell et al, Mol. Endocrinol. 9:659-669 (1995); Tzukerman et al, Mol. Endocrinol. 8:21-30 (1994)). Conversely, tamoxifen functions as an agonist when AF-1 alone is required (McDonnell et al, Mol. Endocrinol. 9:659-669 (1995); Tzukerman et al, Mol. Endocrinol. 8:21-30 (1994)). Subsequently, based on their relative AF-1/AF-2 activity, four mechanistically distinct groups of ER-modulators were defined; full agonists (i.e. estradiol), two distinct classes of partial agonists, represented by tamoxifen and raloxifene, and the pure antagonists, of which ICI182,780 is a representative member (McDonnell et al, Mol. Endocrinol. 9:659-669 (1995); Tzukerman et al, Mol. Endocrinol. 8:21-30 (1994)). These results provide a mechanistic explanation for the observed differences in the biological activities of some ER-modulators and indicate that the mechanism by which ER operates in different tissues is not identical. Interestingly, the agonist activity exhibited by ER-modulators, such as estrogen and tamoxifen, in these in vitro systems reflects their activity in the reproductive tracts of whole animals. This correlation does not extend to bone, however, where estradiol, tamoxifen and raloxifene, which display different degrees of AF-1/AF-2 agonist activity, all effectively protect against bone loss in the ovariectomized rat model. Thus, with the exception of the steroidal pure antiestrogens (ie, ICI182,780), all known classes of ER modulators appear to protect against bone loss in humans and relevant animal models, while they display different degrees of estrogenic activity in other tissues (Chow et al, J. Clin. Invest. 89:74-78 (1992); Love et al, New Engl. J. Med. 326:852-856 (1992); Draper et al, Biochemical Markers of Bone and Lipid Metabolism in Healthy Postmenopausal Women. In:C. Christiansen and B. Biis (eds) Proceedings 1993. Fourth International Symposium on Osteoporosis and Consensus Development Conference, Handelstrykkeriet, Aalborg; Wagner et al, Proc. Natl. Acad. Sci. USA 93:8739-8744 (1996); Black et al, J. Clin. Invest 93:63-69 (1994)).

SUMMARY OF THE INVENTION

The present invention is based on the identification of ER modulators that are mechanistically distinct from modulators such as tamoxifen. These modulators have application in the treatment of a variety of estrogen-dependent diseases and disorders, including breast cancer. These modulators are of particular importance in the treatment of breast cancers that are de novo resistant to tamoxifen or that become resistant with treatment.

Objects and advantages of the invention will be clear from the description that follows.

BRIEF DESCRIPTION OF THE DRAWINGS

FIGS. 2A-2C. GW5638 and GW7604 oppose the agonist activity of estradiol, the partial agonist activity of tamoxifen and the inverse agonist activity of ICI182,780. FIG. 2A. The ability of GW5638 or GW7604 to inhibit the agonist activity of $10^{-8}$M 17-β-estradiol or the partial agonist activity exhibited by $10^{-8}$M tamoxifen was assessed in HepG2 cells transfected with ERwt. FIG. 2B. The ability of GW5638 or GW7604 to inhibit the agonist activity of $10^{-8}$M 17-β-estradiol or the partial agonist activity exhibited by $10^8$M 4-OH tamoxifen was assessed in HepG2 cells transfected with ER-TAFI (McDonnell et al, Mol. Endocrinol. 9:659-669 (1995)). FIG. 2C. Both GW5638 and GW7604 can inhibit the inverse ER-agonist activity of ICI182,780 (ICI) manifest on the C3 promoter when assayed in HepG2 cells at the concentrations indicated. Transfections were normalized for efficiency and cell number by cotransfecting an expression plasmid containing β-galactosidase. The normalized response was obtained by dividing light units by the activity of β-galactosidase as measured in an enzymatic assay. Representative assays are shown in which triplicate transfections were performed. Error bars represent the standard error of the mean (SEM).

FIGS. 3A and 3B. GW5638 protects against bone loss in ovariectomized rats. FIG. 3A. Effect of GW5638 on bone mineral density (BMD) at the lumbar spine (L1-L4) was measured using dual x-ray absorbtiometry. The significance of the difference in BMD between OVX and treated rats was determined using Dunnets's test (*$p \leq 0.005$). The range of the bone mineral densities observed in Sham (shaded bar) and OVX (open bar) animals are indicated. FIG. 3B. The effect of GW5638 on BMD at the proximal metaphysis of the tibia in OVX rats was measured by quantitative computerized tomography (QCT). The significance of the difference in BMD between OVX and treated rats (indicated by the asterisks) was determined using the Turkey-Kramer test ($p \leq 0.05$).

FIG. 13A. ER wt. FIG. 13B. ER-TAFl.

FIG. 15A. MCF-7 cells.

FIG. 15B. Ishikawa cells. FIG. 15C. Ishikawa cells transfected with pRST7ER

FIG. 19A. ICI 182,780. FIG. 19B. GW7604. FIG. 19C. 4-OH tamoxifen.

DETAILED DESCRIPTION OF THE INVENTION

Figure 1A:
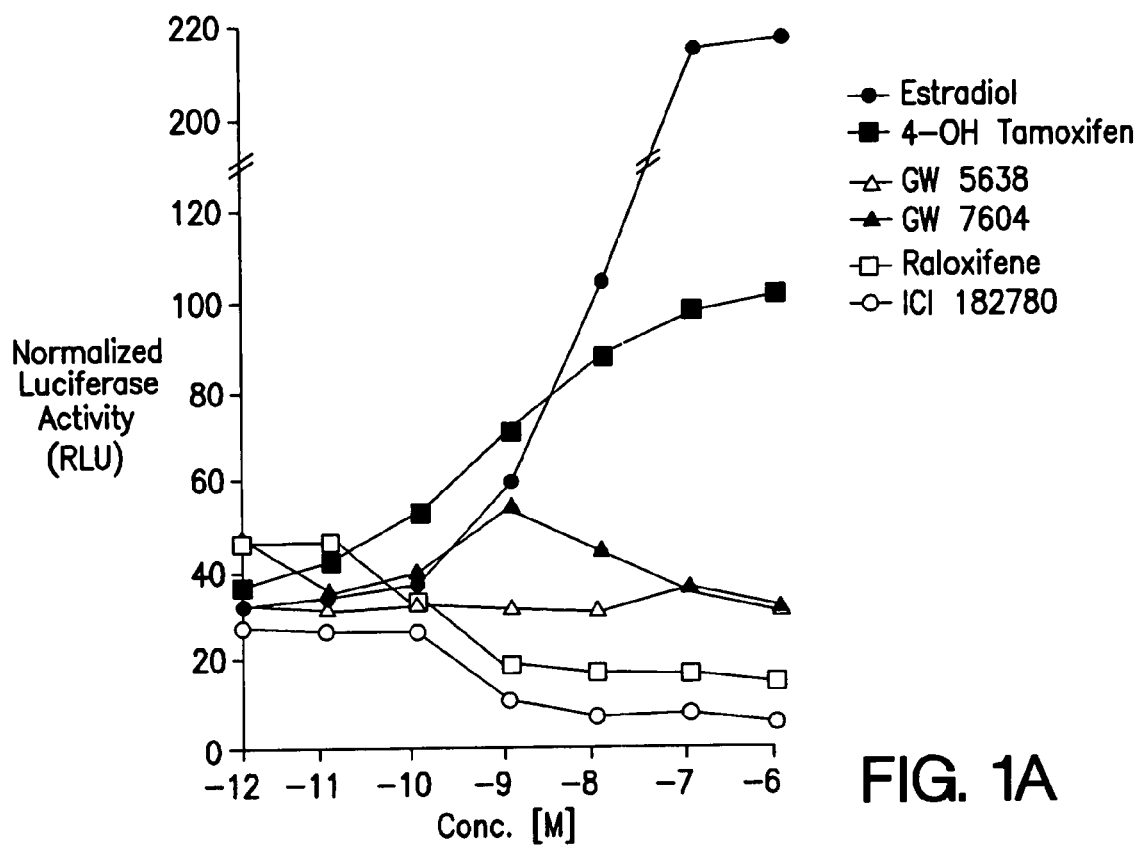
FIGS. 1A and 1B. GW5638 is mechanistically distinct from known classes of ER-modulators. The human C3 promoter (−1807 to +58) fused to the firefly luciferase reporter gene was transfected along with an expression plasmid containing (FIG. 1A) the wild-type human estrogen receptor (ERwt), or (FIG. 1B) a mutated ER in which the AF-2 function had been disrupted (ER-TAFl) into HepG2 cells and tested for transcriptional activation in the presence of increasing concentrations of ER-modulator as indicated. Transfections were normalized for efficiency and cell number by cotransfecting an expression plasmid containing β-galactosidase. The normalized response was obtained by dividing light units by the activity of β-galactosidase as measured in an enzymatic assay. Triplicate transfections were performed. The data shown are representative of multiple experiments performed under similar conditions.

The present invention relates to selective estrogen receptor modulators that possesses tissue-specific ER agonist activity. The modulators of the invention function as agonists in bone and in the cardiovascular system, but not in the uterus. These modulators are mechanistically distinct from, for example, tamoxifen and are useful in the treatment of tumors, such as breast tumors particularly ER positive breast tumors, characterized by de novo or acquired resistance to various estrogen receptor modulators, including tamoxifen. The present modulators are also mechanistically distinct from raloxifene, droloxifene, idoxifene and ICI182,780.

Preferred modulators of the invention are triphenylethylene derivatives, more preferably compounds of Formula I as defined in U.S. Pat. No. 5,681,835, GW5638 and derivatives thereof such as GW7604, being most preferred. These compounds can be prepared as described in U.S. Pat. No. 5,681,835 and by Willson et al (J. Med. Chem. 37:1550 (1994)). The modulators can form pharmaceutically acceptable salts with cations, including alkali metals, such as sodium and potassium, or alkaline earth metals, such as calcium or magnesium, cations.

The modulators of the present invention can be used in the treatment and/or prevention of a variety of disorders or conditions, such as estrogen-stimulated cancers, including uterine cancer, ovarian cancer, colon cancer and breast cancer, cardiovascular disease (in males and females), osteoporosis and arthritic conditions. Other disorders or conditions for which the modulators of the present invention are useful (for both treatment and prevention) include prostatic cancer, infertility (eg as an inducer of ovulation) vasomotor symptoms associated with menopause (eg "hot flashes"), vaginitis, benign proliferative disorders including endometriosis and uterine fibroids, Type II diabetes, macular degeneration, urinary incontinence and Alzheimer's disease (cognitive function). Further, the present compounds can be used as contraceptives in females.

As will be clear from the Examples that follow, GW5638 and derivatives thereof are mechanistically unique modulators. These agents are expected to be superior to, for example, tamoxifen as a first line therapy and as a chemopreventative for estrogen-stimulated cancers, particularly, breast cancer, as they lack uterotrophic activity. These agents have no classical activity on ER and therefore it is anticipated that they will not induce resistance to the same degree as current compounds. Further, these agents can be used to treat patients that respond poorly to other estrogen receptor modulators, including tamoxifen, idoxifene, raloxifene and ICI 182,780, as well as those that initially respond well to such modulators but subsequently fail. In view of the mechanistic uniqueness of the present agents, it is expected that their usage will not result in adverse side effects, such as deep vein thrombosis.

Because of the unique mechanism of action the present modulators, their use as a component of a therapeutic "cocktail", particularly for the treatment of breast cancer, is also contemplated. In this regard, the present modulators can be used in combination with another antiestrogen, a ligand of the retinoic acid or retinoxic X receptor, an antiprogestin such as RU486, an antiandrogen such as casdex or flutamide, vitamin D (or metabolite thereof), a farnesyl transferase inhibitor, a PPAR a or gamma agonist or a MAP kinase inhibitor.

As indicated above, the invention includes the use of the present modulators in prophylaxis as well as in the treatment of established diseases or symptoms. The amount of the modulator required for use will vary with the condition (disease/disorder) and the age and condition of the patient, and will be ultimately at the discretion of the attendant physician (or veterinarian in the case of veterinary applications). In general, however, doses employed for adult human treatment will typically be in the range of 0.001 mg/kg to about 100 mg/kg per day. The desired dose can conveniently be presented in a single dose or as divided doses administered at appropriate intervals, for example as two, three, four or more sub-doses per day.

The present invention also includes pharmaceutical compositions comprising the above-described modulator, or a pharmaceutically acceptable salt thereof, together with one or more pharmaceutically acceptable carriers and, optionally, other therapeutic and/or prophylactic ingredients, including those described above.

Formulations of the present invention can be administered in standard manner for the treatment of the indicated diseases/disorders, such as orally, parenterally, sublingually, transdermally, rectally, via inhalation or via buccal administration. For buccal administration, the composition can take the form (eg dosage unit form) of a tablet or lozenge formulated in conventional manner. For example, tablets and capsules for oral administration can contain conventional excipients such as binding agents, fillers, lubricants, disintegrants and wetting agents. The tablets can be coated according to methods well-known in the art.

Alternatively, the modulators of the present invention can be incorporated into oral liquid preparations such as aqueous or oily suspensions, solutions, emulsions, syrups or elixirs. Moreover, formulations containing these modulators can be presented as a dry product for constitution with water or other suitable vehicle before use. Such liquid preparations can contain conventional additives such as suspending agents, emulsifying agents, preservatives and non-aqueous vehicles.

Such preparations can also be formulated as suppositories, e.g., containing conventional suppository bases such as cocoa butter or other glycerides. Compositions for inhalation can be typically provided in the form of a solution, suspension or emulsion that can be administered as a dry powder or in the form of an aerosol using a conventional propellant such as dichlorodifluoromethane or trichlorofluoromethane. Typical transdermal formulations comprise a conventional aqueous or non-aqueous vehicles, such as creams, ointments, lotions or pastes or are in the form of a medicated plaster, patch or membrane.

Additionally, compositions the present invention can be formulated for parenteral administration by injection or continuous infusion. Formulations for injection can take such forms as suspensions, solutions, or emulsions in oily or aqueous vehicles, and can contain formulatory agents such as suspending, stabilizing and/or dispersing agents. Alternatively, the active ingredient can be in powder form for constitution with a suitable vehicle (e.g., sterile, pyrogen-free water) before use.

The composition according to the invention can also be formulated as a depot preparation. Such long acting formulations can be administered by implantation (for example, subcutaneously or intramuscularly) or by intramuscular injection. Accordingly, the modulators of the invention can be formulated with suitable polymeric or hydrophobic materials (as an emulsion in an acceptable oil, for example), ion exchange resins or as sparingly soluble derivatives or as a sparingly soluble salt, for example.

The identification of GW5638 and GW7604 as agents devoid of classical agonist activity indicates that compounds that "activate" ER (that is, compounds that cause ER to be released from heat schock proteins) and that also do not cause ER degradation, can be used in the treatment of osteoporosis. The discovery of the inability to split the osteoporotic and cardioprotective activities of GW5638 and GW7604 indicates that any compound that binds ER and has either activity (osteoporotic or cardioprotective) will also have the other.

Certain aspects of the present invention are described in greater detail in the non-limiting Examples that follow.

EXAMPLES

The following experimental details are referenced in specific Examples that follow.

Biochemicals

DNA and modification enzymes were obtained from Boehringer Mannheim (Indianapolis, Ind.), New England Biolabs (Beverly, Mass.) or Promega Corp. (Madison, Wis). General laboratory reagents and 17β-estradiol ($E_2$) were purchased from Sigma (SL Louis, Mo.). ICI182,780 was a gift from Zeneca Pharmaceuticals, Macclesfield, United Kingdom. Raloxifene was a gift from Pfizer Pharmaceuticals, Groton, Conn. 4-OH tamoxifen was a gift from Ligand Pharmaceuticals (San Diego, Calif.). GW5638 and GW7604 were prepared as described previously (Wilson et al, J. Med. Chem. 37:1550-1552 (1994)). Antibody H222 is available from Abbott Laboratories.

Cell Culture and Cotransfection Assays

HepG2 cells were maintained in Modified Eagles Medium (MEM) (Life Technologies, Grand Island, N.Y.) plus 10% Fetal Calf Serum (FCS) (Life Technologies). Cells were plated in 24 well plates (coated with gelatin) 24 hours prior to transfection. DNA was introduced into the cells using Lipofectin (Life Technologies). Briefly, triplicate transfections were performed using 3 μg of total DNA. For standard transfections, 500 ng of pCMV-β-Gal (normalization vector), 1500 ng reporter (variable) and 1000 ng receptor (pRST7-hER (Dana et al, Mol. Endocrinol. 8:1193-1207 (1994)) were used for each triplicate. Incubation of the cells with Lipofectin proceeded for 3 hrs, at which time media was removed, cells were washed with PBS and then induced with the appropriate hormone diluted in phenol red-free media containing 10% charcoal stripped CS (Cyclone Inc.). Incubation with hormone continued for 48 hrs, after which cells were lysed and assayed for luciferase and β-galactosidase activity as previously described (Norris et al, JBC 270:22777-22782 (1995)).

Uterotrophic Assay in Immature Rats

Twenty-one day old female Sprague-Dawley rats (30-35 gms) were obtained from Harlan or Taconic Laboratories. Animals were sorted randomly into treatment groups of five, and average weights were recorded for each treatment group. Weights were recorded on each treatment day. GW5638 or tamoxifen was prepared in 100% ETOH as a 10× stock solution and stored at −70° C. until day of dosing. On day of dosing, drug was diluted in 0.5% methyl cellulose, viscosity of 2% at 25° C.:400 centipoises (Sigma, St. Louis, Mo.)). Oral dosing by gavage was based on a total volume of 10 ml/kg body weight. Estradiol (Sigma, St. Louis, Mo.) was prepared in sesame oil, mixed in a glass homogenize (either dissolved or in suspension), aliquot and frozen at −70° C. until dosing. Subcutaneous dosing was based on a total of 2 ml/kg body weight. Animals were gavaged (GW5638) or injected (estradiol) for 3 days. On day 4, animals were sacrificed by $CO_2$ asphyxiation, body weights were obtained and uteri were removed, blotted and weighed. Data were expressed as uterine weight/body weight.

Bone Mineral Density Studies

Animal preparation. Sprague-Dawley rats, 90-days of age, were anesthetized with isofluorane (4% induction, 2% maintenance), ovariectomized (OVX) or sham operated (SO) and randomly assigned to groups (n=7) treated from day 1 to day 28 post-surgery by oral gavage with vehicle alone, estradiol or GW5638 in 0.5% methyl cellulose. At sacrifice, animals were euthanized with $CO_2$, body weights were recorded and the uteri were removed and weighed. Uterus, vagina and mammary tissue were fixed in 10% neutral buffered formalin. Samples for histologic processing were taken from the mid-point of each uterine horn. Tissue samples were embedded in paraffin, stained with haematoxylin and eosin and evaluated microscopically. Lumbar vertebrae and both left and right tibiae were excised. Total blood cholesterol was measured (Roche Biomedical Laboratories).

Dual energy X-ray absorptiometry (DEXA). A Hologic QDR-2000 bone densitometer with a regional high-resolution software package was used for DEXA analysis. Default scan length, width, line spacing and point resolution were set at 2, 0.75, 0.01 and 0.005 inches, respectively. The densitometer was calibrated daily using a hydroxyapatite spine platform. Excised tibiae were placed in a 1 cm deep water bath with tibia and fibula positioned horizontally. For in vivo scans, rats were anaesthetized with isofluorane and placed in a supine position with the spine parallel to the long axis of the densitometer table. The scan leg was taped in position parallel to the long axis of the table and the tibia was scanned to the junction with the femur. A region of interest (ROI) in the tibia was analyzed with sub-regional software, focusing on a 2 mm wide zone beginning 3 mm distal to the growth plate.

Peripheral quantitative computed tomography (pQCT). CT scans were performed on a PQCT (XCT-960A, Norland). Four to five millimeter sections were scanned with a voxel size of E (0.148 mm) and a step of 0.5 mm. A 3-5 mm section distal to the growth plate was analyzed using contmode, 2/peelmode, 5/cortmode. Measurements of total, trabecular and cortical bone mineral density were obtained. The excised tibiae were placed in a 1 cm deep water bath with the tibia and fibula positioned horizontally to ensure that the bone could be scanned vertically. Rats were anaesthetized with isofluorane and the leg positioned so that the image of the femur-tibia and tibia-fibula junctions on scout view could be located and utilized as landmarks for CT scans.

Example 1

Identification of Novel ER-Modulators

A series of in vitro screens have been developed that permit the classification of ER-modulators into four mechanistically distinct groups (Tzukerman et al, Mol. Endocrinol. 8:21-30 (1994)). Specifically, an assay in liver HepG2 cells was reconstituted in which the ability of a compound to regulate the transcriptional activity of the estrogen responsive complement 3 (C3) promoter is evaluated in the presence of either wild type ER (ERwt) or a receptor mutant, ER-TAF1, in which the AF-2 function has been destroyed. Using these assays, it has been possible to derive "fingerprints" of known ER-modulators (McDonnell et al, Mol. Endocrinol. 9:659-669 (1995)). Although these assays do not reflect exactly the environment of ER in vivo, the performance of compounds in these assays is sufficient to separate them into groups, each of which manifests unique activities in vivo.

A series of triphenylethylene derived ER-ligands were synthesized (Willson et al, J. Med. Chem. 37:1550-1552 (1994)). Preliminary analysis of these compounds in vivo indicated that the relative activities of these compounds in bone and in the uterus were not identical, reflecting possible mechanistic differences (Willson et al, J. Med. Chem. 37:1550-1552 (1994)). Consequently, a blinded assay of these compounds was performed on ERwt in HepG2 cells on the C3 promoter and it was determined that all but two compounds were mechanistically indistinguishable from tamoxifen. Two compounds however, GW5638 and GW7604, demonstrated a sufficiently different profile in this system from other ER ligands to warrant further investigation. Interestingly, these compounds are structurally identical to each other except that GW7604 is the 4-hydroxylated version of GW5638 (Table 1). Using an in vitro competitive radioligand binding assay, both of these compounds were demonstrated to exhibit high affinity ER-interactions. Specifically, GW5638 and GW7604 demonstrated $K_i$ values of 50.4 nM (+/−5.4) and 15.5nM (+/−1.4), respectively. Under the same conditions 17-β-estradiol was shown to have a $K_i$ value of 6.3nM (+/−0.4). Although the metabolism of GW5638 has not been studied, it is likely that it is converted to the higher affinity compound GW7604 in vivo in the same manner as tamoxifen is converted to the higher affinity metabolite 4-OH tamoxifen (Jordan et al, J. Endocrinology 75:305-316 (1977)). A comparison of the agonist activity of these compounds to representative members of each of the four established groups of ER-ligands is shown in FIG. 1A. In this assay, tamoxifen acts as a partial agonist of ER when assayed on the C3 promoter, achieving 45% the efficacy of estradiol. When analyzed in the same manner, raloxifene and the pure antagonist ICI182,780 do not demonstrate agonist activity but inhibit the basal transcriptional activity of the C3 promoter. Recently, it has been determined that the basal activity of the C3 promoter is ER-dependent, though ligand independent (Norris et al, Molecular Endocrinology 10:1605-1616 (1996)) . Since both raloxifene and ICI182, 780 inhibit ligand-dependent and -independent activation of ER, they appear to be operating as "inverse agonists" in this environment. However, both GW5638 and its putative metabolite GW7604 do not demonstrate any agonist or antagonist activity on this promoter displaying a "fingerprint" previously unrecognized. It was concluded that, in an environment where tamoxifen displays partial agonist activity, the tamoxifen analogs GW5638 and GW7604 are functionally inactive.

Figure 1B:
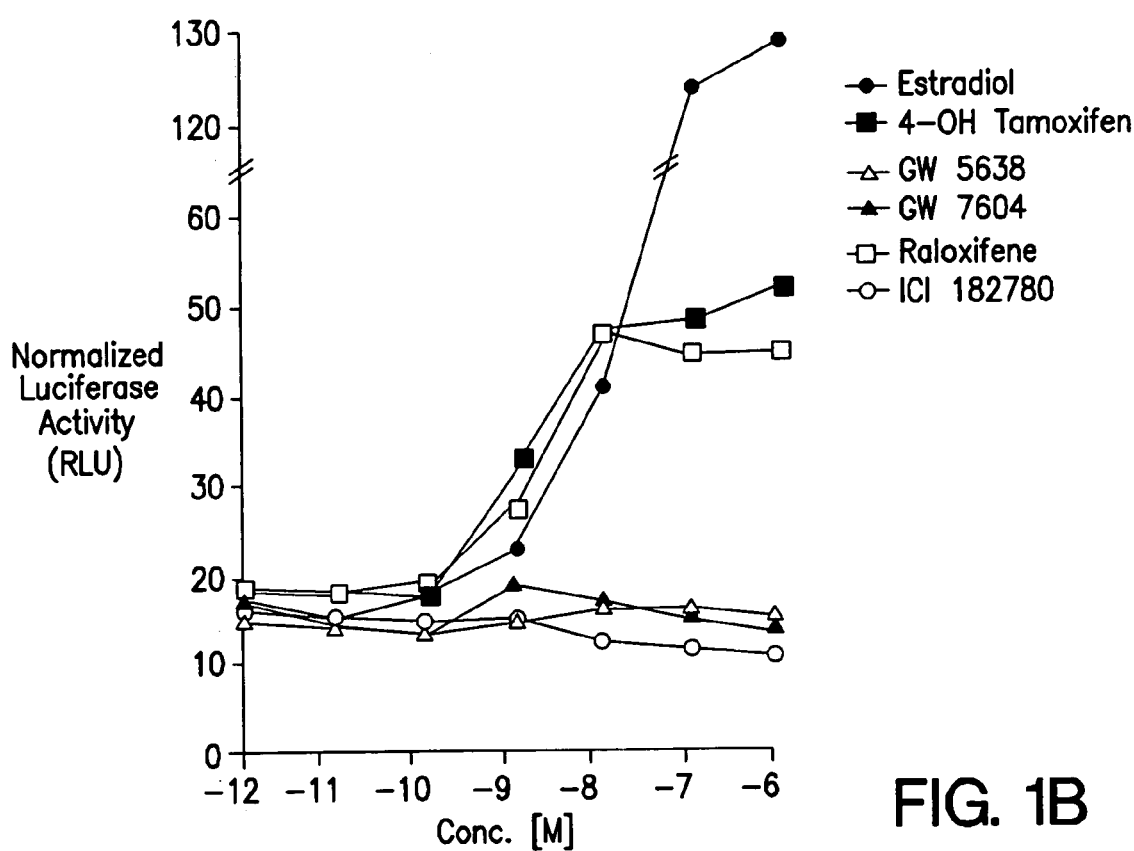

Although raloxifene and ICI182,780 behaved analogously on ERwt, they are mechanistically distinct (McDonnell et al, Mol. Endocrinol. 9:659-669 (1995); Dauvois et al, Proc. Natl. Acad. Sci. USA 89:4037-4041 (1992); Dauvois et al, J. Cell. Sci. 106:1377-1388 (1993)). When assayed on a mutant ER (ER-TAF1), in which the AF-2 activation sequence has been disrupted, raloxifene behaves like tamoxifen, exhibiting 40% the agonist activity of estradiol (FIG. 1B). In this assay ICI182,780, GW 5638 and GW7604 are functionally inactive. These data indicate that GW5638 (and GW7604), function in a manner which is distinct from the previously defined classes of ER-mixed agonists and antagonists (McDonnell et al, Mol. Endocrinol. 9:659-669 (1995)).

One possible, though unlikely, explanation for these initial results is that the compounds were metabolized (or in some way prevented from binding to the receptor) thus explaining their inactivity in this assay. This issue was addressed by assessing the ability of GW5638 and GW7604 to inhibit the agonist activity of estradiol and tamoxifen exhibited on ERwt and ER-TAF1, respectively, and to reverse the inverse agonist activity of ICI182,780. As shown in FIG. 2A, estradiol functioned as a full agonist and tamoxifen functioned as a partial agonist on ERwt when assayed on the C3 promoter in HepG2 cells. Importantly, the agonist activity manifested by tamoxifen or estradiol was inhibited by both GW7604 and GW5638. Thus, these compounds were functioning as antagonists on the receptor in a manner distinct from tamoxifen. A similar analysis was performed using ER-TAF1 in place of ERwt (FIG. 2B). As expected, both GW5638 and GW7604 were capable of inhibiting estradiol- and tamoxifen-induced ER-TAF1 transcriptional activity. Interestingly, raloxifene exhibits partial agonist activity on ER-TAF1 (FIG. 1B); an activity which is inhibited by both GW5638 and GW7604. Cumulatively, these data indicate that GW5638 and its putative in vivo metabolite, GW7604, are mechanistically unique ER-modulators which do not display agonist activity in vitro but which can inhibit the agonist activity of the estradiol, tamoxifen and raloxifene. Although their profile in some of these assays resembles that of the pure antagonist class of ligands, these compounds are distinct from the steroidal antagonists like ICI182,780 as they do not display inverse agonist activity (FIG. 1A).

In order to confirm that GW5638 and GW7604 are mechanistically distinct from ICI182,780, the ability of these compounds to reverse the inverse agonist activity demonstrated by ICI182,780 was measured. The results of this analysis are shown in FIG. 2C. Specifically, it was observed that the basal activity of the human C3 promoter was suppressed 10-fold upon addition of ICI182,780 and that this could be completely reversed by co-addition of GW7604 and partially reversed by GW5638.

One possible explanation for the mechanistic differences observed is that GW5638 and GW7604 interact with ER and inhibit its ability to interact with DNA. This was addressed using a modified ER (ER-VP16) to report on the nuclear localization and the DNA binding status of ER within a cell following ligand binding. This modified protein behaves exactly like ER in all respects except it activates transcription upon interaction with an estrogen response element (ERE) independent of the nature of the bound ligand (Mc- Donnell et al, Mol. Endocrinol. 9:659-669 (1995)). Using this reagent, it was shown that all classes of ER-ligands, including ICI182,780, GW5638 and GW7604 facilitate efficient interactions of ER with target DNA (McDonnell et al, Mol. Endocrinol. 9:659-669 (1995)).

Thus, GW5638 and GW7604 interact with ER in vivo and demonstrate a pharmacology that is distinct from other known ER-modulators. It is implied therefore, that the unique properties of GW5638 and GW7604 are manifest at some step downstream of DNA binding. Because of the unique properties of these compounds, a series of whole animal studies to examine their activity in the skeletal, cardiovascular and reproductive systems was initiated.

Example 2

Prevention of Ovariectomized Induced Bone Loss in Rats

There is now strong evidence that both tamoxifen and raloxifene prevent bone loss in preclinical models of postmenopausal osteoporosis (Love et al, New Engl. J. Med. 326:852-856 (1992); Love et al, Ann. Intern. Med. 115:860-864 (1991); Black et al, J. Clin. Invest 93:63-69 (1994)). However the mechanism of action of these compounds in bone has not been defined. The fate of bone in the patients treated with the pure antagonist ICI182,780 is unclear at the present time though data from preclinical rat models suggest that it is not an agonist in this tissue (Gallagher et al, Endocrinology 133:2787-2791 (1993)). This has led to the hypothesis that the partial agonist activity of tamoxifen and raloxifene is required for bone protection (Love et al, New Engl. J. Med. 326:852-856 (1992); Black et al, J. Clin. Invest 93:63-69 (1994)). Previous work demonstrating that both tamoxifen and raloxifene can function as equally effective agonists in some cell and promoter contexts supports this idea (McDonnell et al, Mol. Endocrinol. 9:659-669 (1995); McDonnell et al, Mol. Endocrinol. 9:659-669 (1995)) However, GW5638 provides a new tool with which to address this issue. This compound, which does not manifest classical agonist activity in any of the in vitro assays, was assayed for its ability to inhibit bone loss in ovariectomized rats. Specifically, bone mineral density (BMD) in both the lumbar spine and tibia of 90-day old ovariectomized rats was assayed following oral administration for 28 days of either 17β-estradiol or increasing doses of GW5638. The results shown in FIG. 3A indicate that significant bone loss occurred in the lumbar spines of ovariectomized (OVX) animals over the course of the 28 day study when compared to control sham-operated animals, whereas BMD was maintained in OVX rats treated with estradiol. Significantly, GW5638 demonstrated dose-dependent bone protective activity, being as effective as estradiol at a concentration of 3 μmol/kg(1 mg/kg). This is similar to the dose of tamoxifen required for bone protection in the same model (Love et al, New Engl. J. Med. 326:852-856 (1992); Black et al, J. Clin. Invest 93:63-69 (1994); Yang et al, Endocrinology 137: 2075-2084 (1996)). The bone protective activity observed was not restricted to the lumbar spine as analogous results were obtained when tibial BMD was accessed (FIG. 3B). Specifically, using the same experimental protocol, it was demonstrated that GW5638 was effective at maintaining total bone mass with a very pronounced effect in the trabecular compartment. This was interesting in light of the fact that estrogen has previously been shown to regulate bone turnover in this compartment (Gallagher et al, Endocrinology 133:2787-2791 (1993)). Together, these data indicate that GW5638, a compound devoid of classical ER-agonist activity, when assayed in vitro, functions as an efficient ER agonist in bone.

Figure 4:
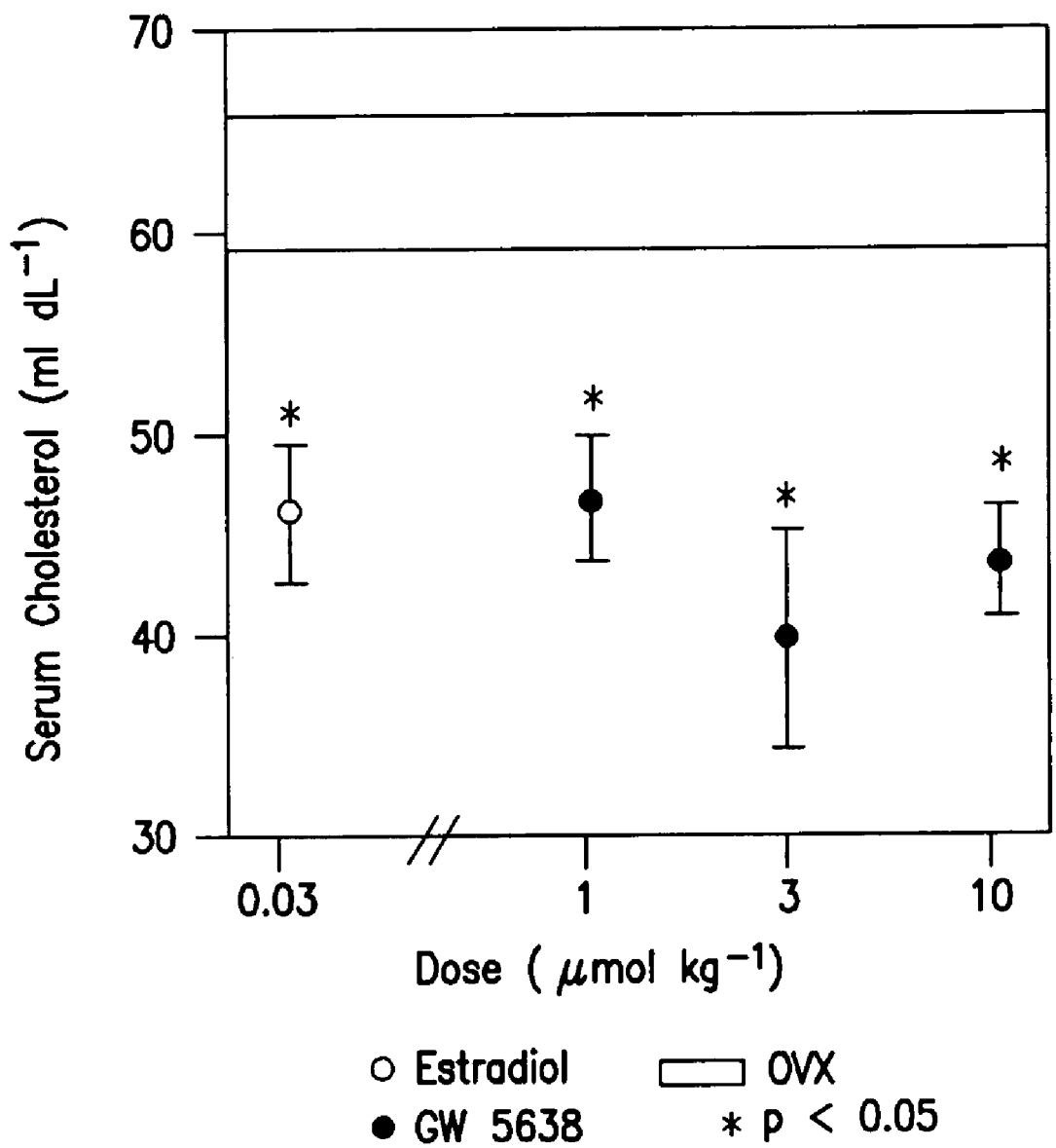
FIG. 4. GW5638 suppresses ovariectomy-induced elevations in serum cholesterol. Serum cholesterol measurements were performed in blood extracted from groups of 90-day old ovariectomized rats which were treated with either estradiol or GW5038 as indicated. Each point represents the mean serum cholesterol (±SEM) for OVX control (n=7), estradiol (n=7) and GW5638 (n=7) as indicated. Asterisks indicate groups significantly different from the OVX control. The range of serum cholesterol in OVX animal are indicated (open bar).

It has been shown that compounds that function as ER agonists in bone, such as estradiol, tamoxifen and raloxifene, can also suppress the rise in serum cholesterol associated with ovariectomy (Love et al, Ann. Intern. Med. 115:860-864 (1991); Black et al, J. Clin. Invest 93:63-69 (1994)). This observation has led to the suggestion that the mechanism of ER activity in bone and the cardiovascular system is very similar. Although it is not clear whether the observed suppression of serum cholesterol levels is sufficient to explain the decrease in mortality from cardiovascular disease in postmenopausal women on estrogen replacement therapy, it is accepted as a marker of estrogen action in the cardiovascular system. To address this issue the total serum cholesterol level was assayed in ovariectomized rats treated with estradiol or GW5638 for 28 days. The results shown in FIG. 4 indicate that even at the lowest concentration tested, GW5638 was as effective as estradiol in decreasing serum cholesterol levels.

Example 3

GW5638 as a Uterine Sparing ER-Modulator

Figure 5:
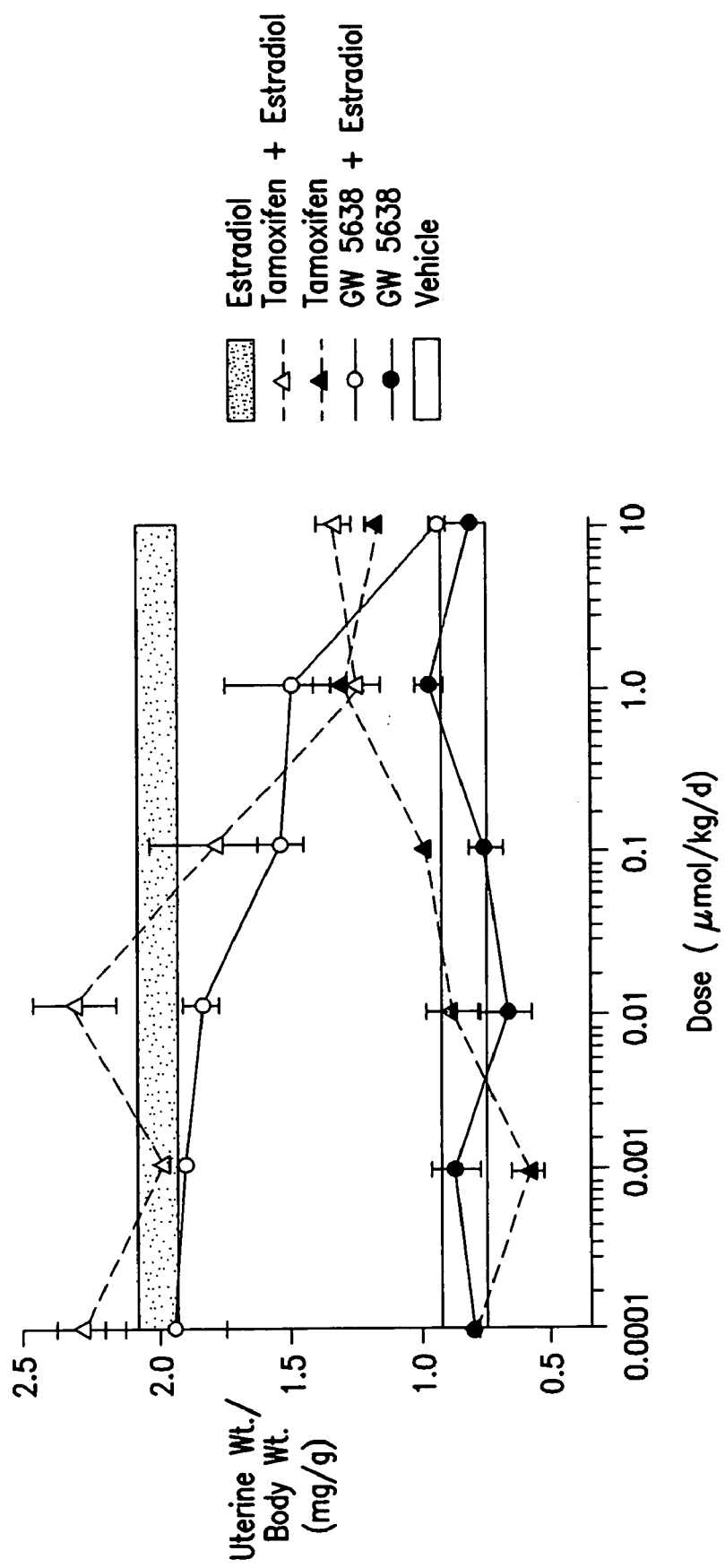
FIG. 5. GW5638 does not display ER agonist activity in the immature rat uterus. Groups of 21-day old rats were treated orally with either vehicle alone, GW5638 or tamoxifen as single agents or GW5638 or tamoxifen in the presence of estradiol. The data shown represent the mean value (±SEM). The range in measurements made in estradiol treated (shaded bar) and sham operated animals (open bar) are indicated.

To extend the examination of the tissue specificity of GW5638, a comprehensive analysis of the uterotrophic activity of this compound was performed. In the initial series of experiments, the activities of GW5638 and tamoxifen in the uteri of 21 day old immature rats were compared. In this assay, uterine wet weight was used as a measure of ER-agonist activity in this tissue (FIG. 5). When administered orally, as a single agent, GW5638 did not display any significant activity over control Note in particular that this compound is inactive in this assay at 10 μm/kg/d, three times the amount required for bone protection (FIG. 3). In contrast, tamoxifen demonstrated uterotrophic activity at doses as low as 0.1 μmol/kg/d. These studies were extended to show that GW5638, but not tamoxifen, could completely inhibit the agonist activity of estradiol in these rats confirming that this compound is a pure antagonist in this tissue under the conditions of the assay.

Figure 6:
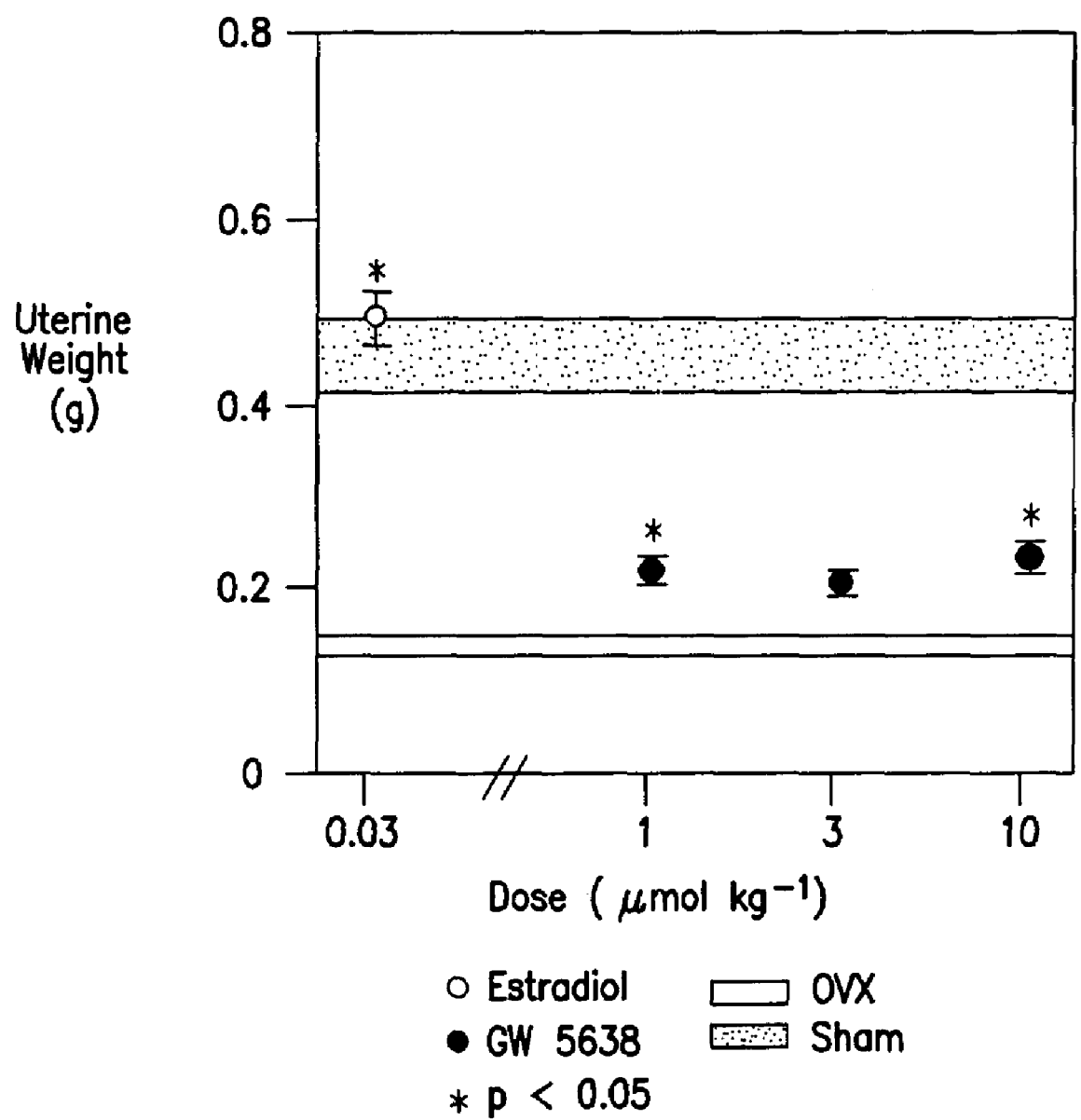
FIG. 6. Effect of GW5638 on uterine wet weight in ovariectomized rats. Groups of sham-operated or ovariectomized 90-day old rats were treated for 28 days with vehicle alone, estradiol or GW5638. The results shown represent the mean uterine wet weight (±SEM) for 7 rats per group. The range in measurements made in sham operated (shaded bar) and OVX (open bar) animals (open bar) are indicated.
Figure 7A:
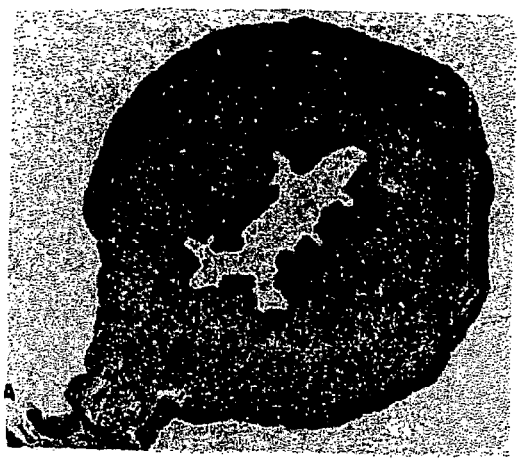
FIGS. 7A-7F. Effect of GW5638 on uterine histology in ovariectomized rats. Comparative histology (Low Magnification) of uteri from 90-day old rats which were (FIG. 7A) sham-operated, (FIG. 7B) ovariectomized, (FIG. 7C) ovariectomized plus estradiol, or ovariectomized plus (FIG. D) 1 µg/kg, (FIG. 7E) 3 µm/kg or (FIG. 7F) 10 µg/kg of GW5638.
Figure 7B:
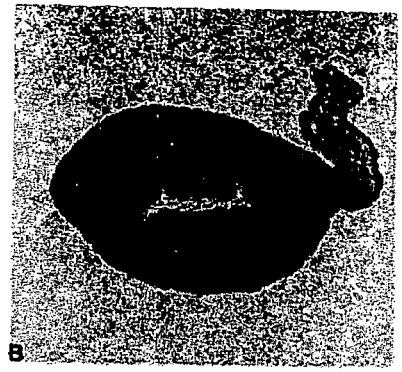
Figure 7C:
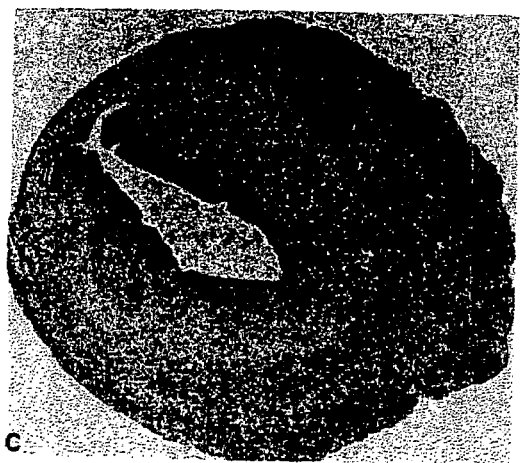
Figure 7D:
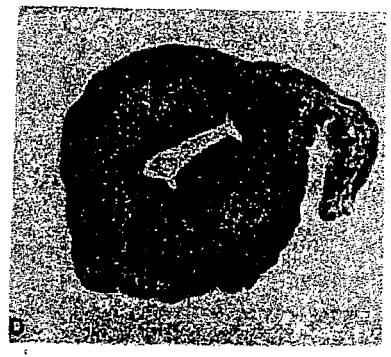
Figure 7E:
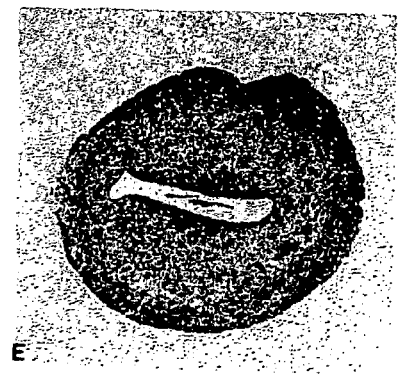
Figure 7F:
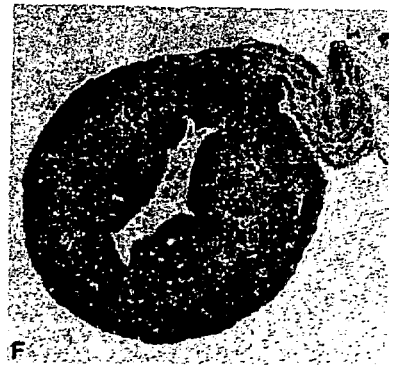
Figure 8A:
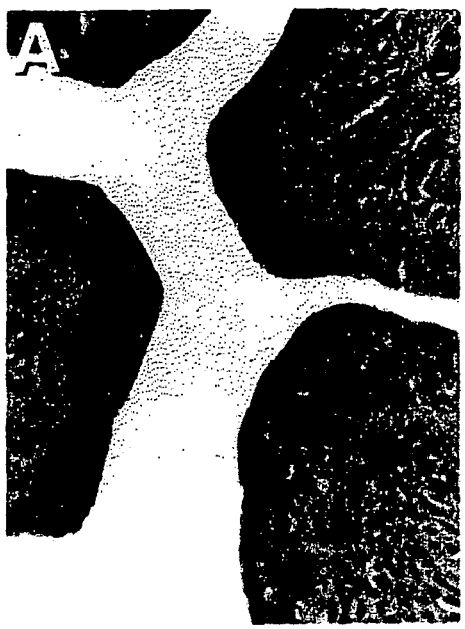
FIGS. 8A-8D. Effect of GW5638 on uterine histology in ovariectomized rats. Comparative histology of uteri from 90-day old rats which were (FIG. 8A) sham-operated, (FIG. 8B) ovariectomized, (FIG. 8C) ovariectomized plus estradiol, or ovariectomized plus (FIG. 8D) 10 µm/kg of GW5638. Photographs were taken at 150× magnification and subsequently enlarged to a final magnification of 600×.
Figure 8B:
Figure 8C:
Figure 8D:

In the second series of experiments, uterotrophic activity following 28 day treatments with either GW5638 or estradiol was evaluated in 90-day old ovariectomized (OVX) rats. The results of this analysis, shown in FIG. 6A, indicate that at doses up to three times that required for bone protection, GW5638 displays minimal uterotrophic activity. Importantly, however, no significant differences were noted in total body weight of OVX rats treated with GW5638 versus sham operated animals. A very small, dose independent, increase was observed in uterine wet weight over OVX. This is similar to what has been reported by others in rats treated with raloxifene, where the activity has been attributed to an increase in water imbibition (Kedar et al, Lancet 343:1318-1321 (1994); Love et al, Ann. Intern. Med. 115:860-864 (1991); Black et al, J. Clin. Invest 93:63-69 (1994)).

In addition to measurements of uterine wet weight, a histological examination of the uteri harvested from the same animals was performed (FIGS. 7A-7F (low magnification) and FIGS. 8A-8D (high magnification)). In this analysis, the uterine epithelial cells in rats treated with GW5638 exhibited a dose-related hypertrophy, while the stroma demonstrated a marginal increase in intercellular connective tissue and ground substance. At the highest doses of GW5638 (3-fold higher than was required for bone protection), the epithelial hypertrophy observed was comparable to that of estradiol treated uteri whereas the stromal response and eosinophilic infiltration was less than observed in estradiol treated rats (compare FIGS. 8C and 8D). Cumulatively, these data indicate that GW5638 possesses marginal ER-agonist activity in the uterus, whereas, in bone it functions as an ER-agonist. Thus, GW5638 is a unique ER modulator that manifests ER agonist and antagonist activity in a tissue-selective manner.

Example 4

Effect of Antiestrogen Treatment on Breast Cancer Tumors in Nude Mice

Figure 9:
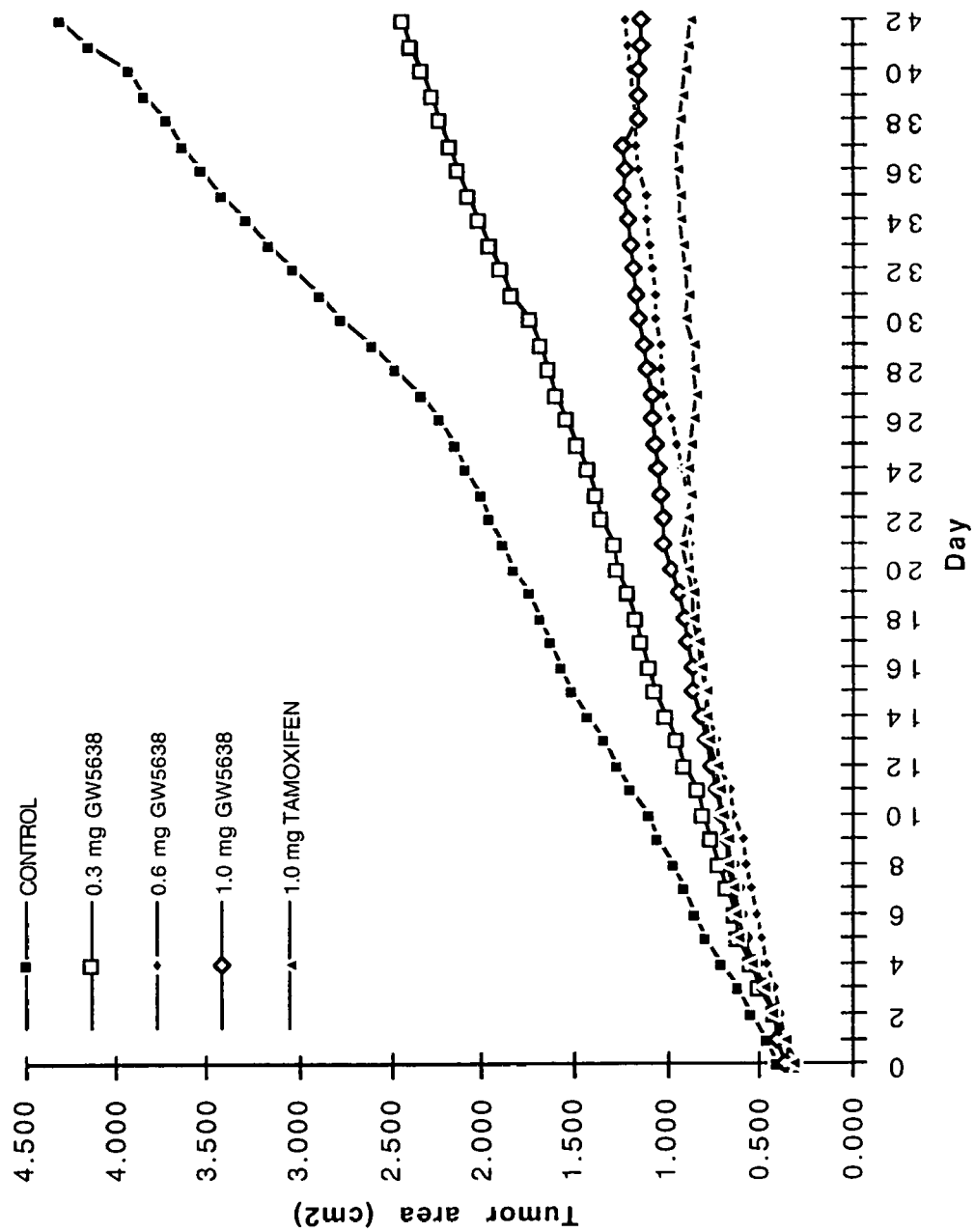
FIG. 9. Effect of anti-estrogen treatment on MCF-7 breast cancer tumors in nude mice. Day 0 indicates the first day of treatment, 2 weeks after innoculation of tumors, statistical analysis revealed that each treatment group had a significant effect over control (ANOVA, p<0.5) and there was no significant difference between the two highest doses of GW5638 and tamoxifen.

This study was conducted using tumor cells derived from the MCF-7 breast cancer line. This line is estrogen and progesterone receptor positive, dependent upon hormone and sensitive to antihormones. The tumor cells were inoculated into the flank of ovariectomized, athymic BALB/c Urd nunu mice. The mice were supplemented with slow release estrogen pellets. Animals were given subcutaneous daily injections as indicated below:

Group 1: control (corn oil)
Group 2: 0.3 mg GW5638
Group 3: 0.6 mg GW5638
Group 4: 1.0 mg GW5638
Group 5: 1.0 mg tamoxifen Using calipers, tumors were measured in 2 dimensions, where tumor area=½×w/2×π. The results are shown in FIG. 9.

Example 5

Dose Response Study

The goal of this study was to compare the maximally effective dose of GW5638 to tamoxifen in terms of ability to inhibit the growth of MCF-7 breast cancer tumors in nude mice.

10 OVX donor mice were injected with 5 million MCF-7 cells. The resulting tumors were transplanted to recipient mice. All animals were given slow release estradiol pellets.

When experimental mice had measurable tumors, daily dosing, via subcutaneous 0.1 ml injections, was begun as follows:

Group 1: control (corn oil)
Group 2: 0.3 mg GW5638
Group 3: 0.6 mg GW5638
Group 4: 1.0 mg GW5638
Group 5: 1.0 mg tamoxifen Tumors were measured daily with calipers, and the area calculated as follows:

Area=½×w/2×π.

Figure 10:
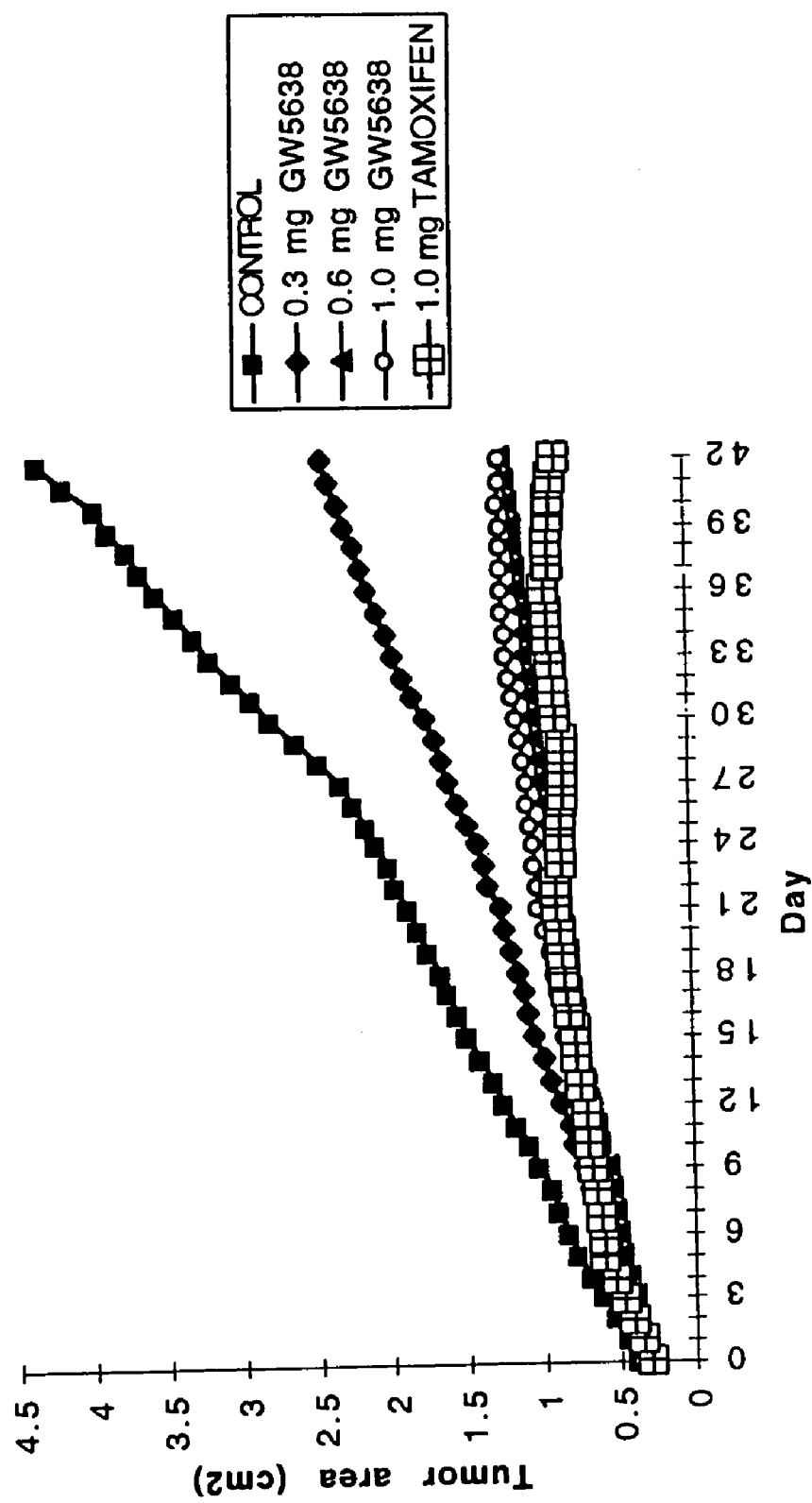
FIG. 10. Dose response study.

After 8 weeks, tumor growth was compared among the groups. All treatment groups inhibited tumor growth (with statistical significance) as compared to control. The two upper doses of GW5G38, 0.6 mg and 1.0 mg, were indistinguishable from the 1.0 mg tamoxifen (see FIG. 10).

Example 6

LCC2 Study

MCF-7/LCC2 is a cell line (from the Lombardi Cancer Center) which is estrogen independent, though sensitive, and tamoxifen resistant. This experiment was conducted to determine the ability of GW5638 to retard the growth of this cell line in nude mice relative to control or tamoxifen treated tumors.

40 OVX mice were prepared to accept cells and grouped as follows:

Group 1: control
Group 2: estrogen pellet
Group 3: 1.0 mg tamoxifen
Group 4: 1.0 mg compound 5638

Control animals received nothing and groups 3 and 4 received 0.1 ml injections in corn oil every three days. Tumors were measured Q3 days with calipers, and the area calculated as follows:

Area=½×w/2×π.

Figure 11:
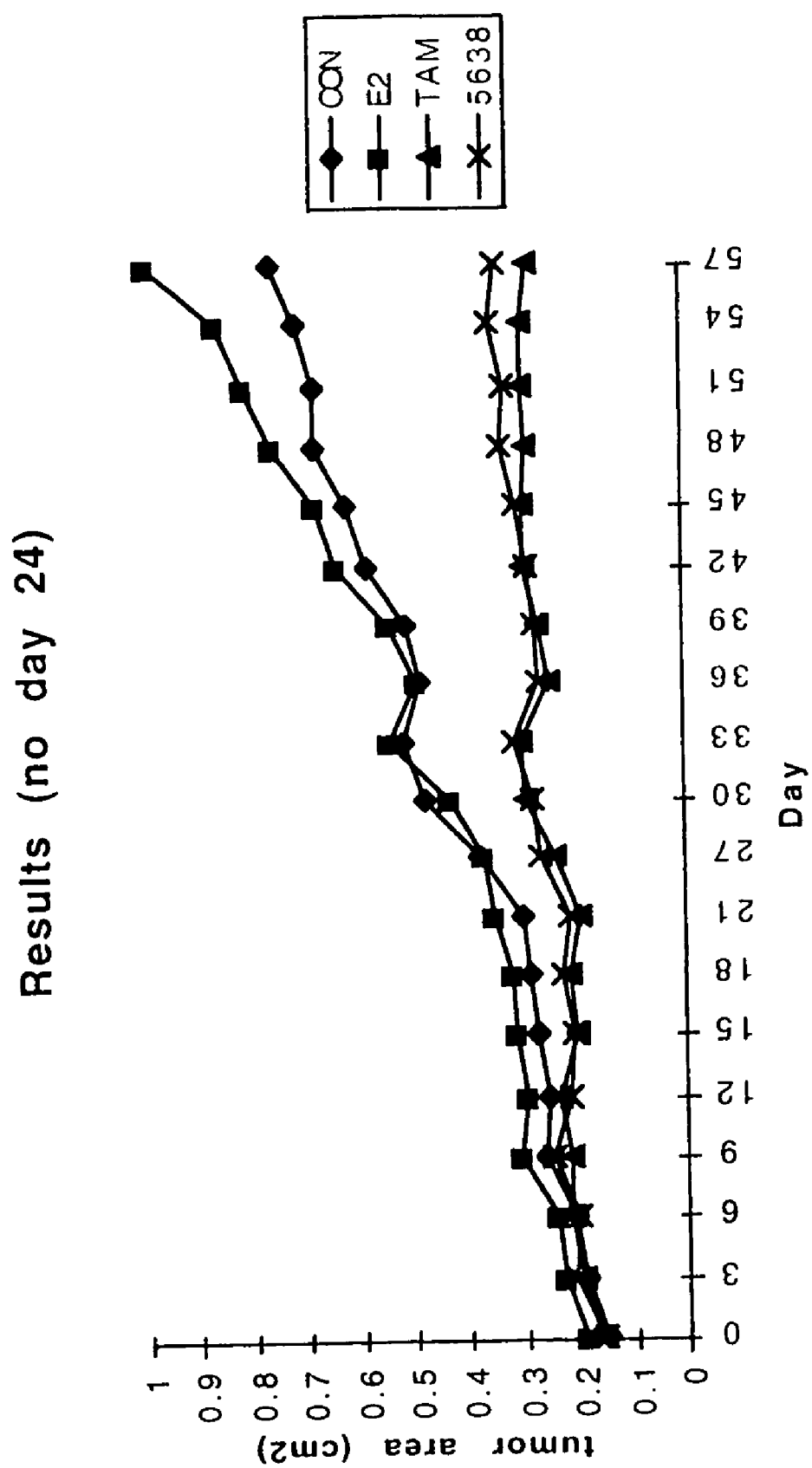
FIG. 11. LCC2 study.

After 8 weeks, tumor growth was compared among groups. In contrast to what was expected, the tumor did not appear to be responsive to estrogen. Additionally, the tumor seemed sensitive to tamoxifen, despite its predicted tamoxifen resistance. Both tamoxifen and GW5638 were able to equally inhibit growth of this tumor (see FIG. 11).

Example 7

GW7604 Functions as an Antiestrogen in MCF-7 Breast Cancer Cells

Figure 12:
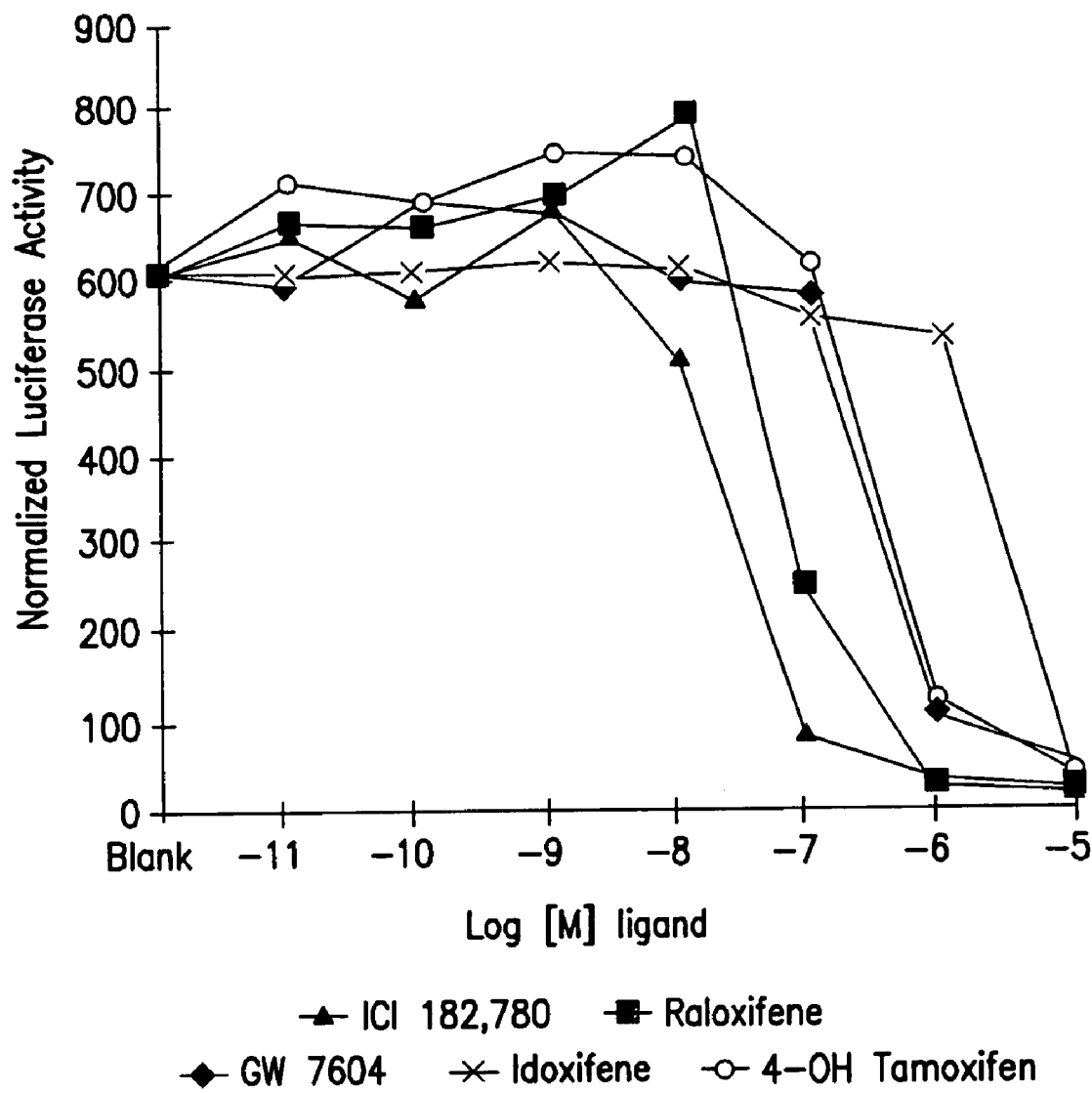
FIG. 12. GW7604 functions as an antiestrogen in MCF-7 breast cancer cells.

Human breast cancer MCF-7 cells were transiently cotransfected with 0.9 μg/ml of human ER expression vector together with 2 μg/ml of the C3-Luc reporter plasmid and 0.1 μg/ml of pRSV-β-galactosidase expression vector (as an internal control for transfection efficiency). Upon transfection, cells were incubated for 48 h in the presence of 17-β-estradiol and increasing concentrations of each antagonist as indicated. Subsequently, the transfected cells were assayed for luciferase and β-galactosidase activity. The normalized luciferase activity was calculated by dividing the raw luciferase ($\times 10^4$ U) for each point by the β-galactosidase activity [($A415 \times 10^5$)/time in minutes]. With reference to FIG. 12, each data point in this experiment represents the average of triplicate determinations of the transcriptional activity under given experimental conditions. The average coefficient of variation at each hormone concentration was <10%.

Example 8

Figure 13A:
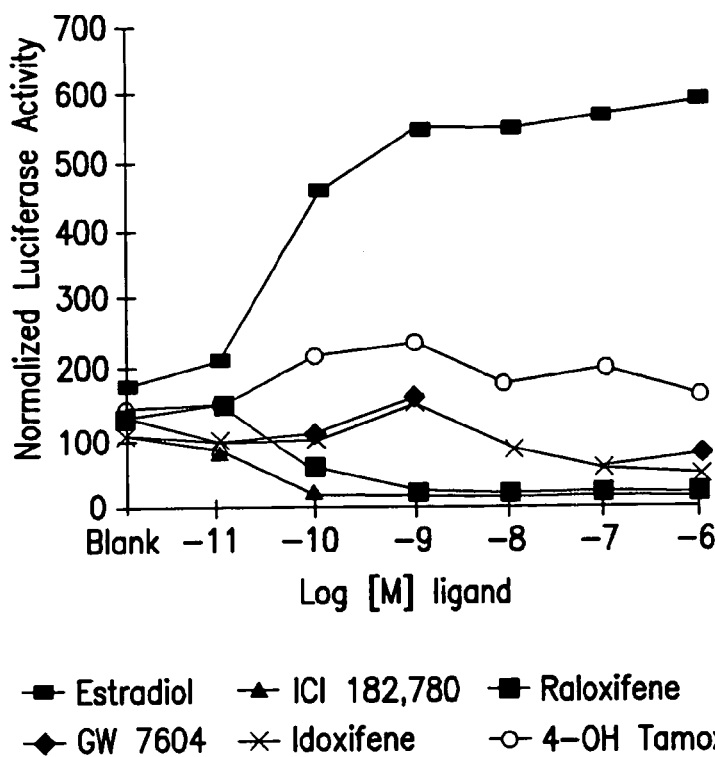
FIGS. 13A and 13B: Analysis of the effect of specific ER mutations on the pharmacology of antiestrogens reveals additional mechanistic complexity.
Figure 13B:
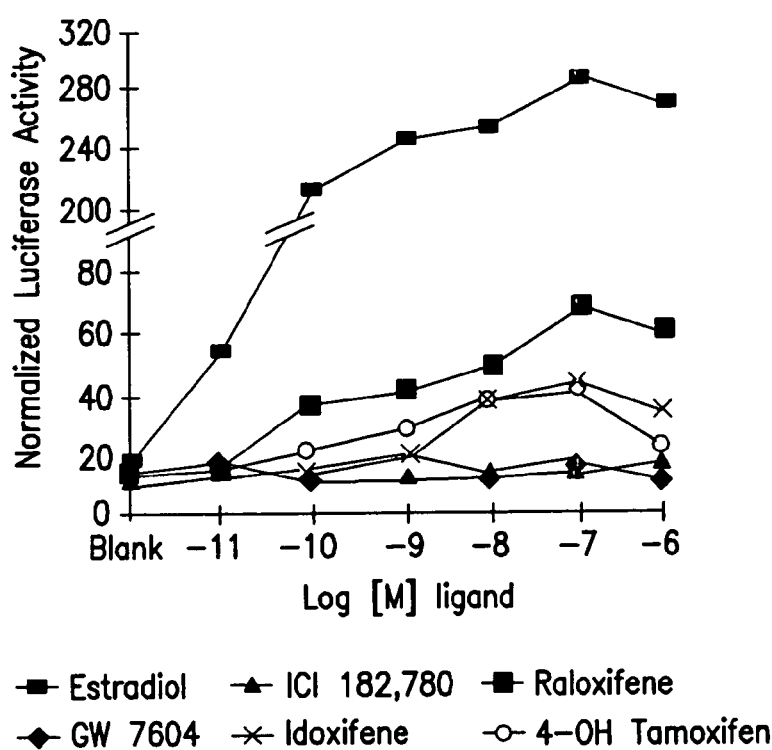

Analysis of the Effect of Specific ER Mutations on the Pharmacology of Antiestrogens Reveals Additional Mechanistic Complexity Human hepatocellular carcinoma HepG2 cells were transiently transfected with 0.9 μg/ml of a vector expressing either human ER (pRST7ER) (see FIG. 13A) or an ER mutant (ER-TAF1) (see FIG. 13B) in which the AF-2 function has been inactivated (ER-TAF1) together with 2 μg/ml of the estrogen-responsive complement 3 (C3) promoter fused to luciferase gene; 0.1 μg/ml of pRSV-β-galactosidase expression vector (as an internal control for transfection efficiency). Upon transfection, cells were incubated for 48 h in the presence of solvent alone or increasing concentrations of estradiol or antiestrogens as indicated. Subsequently, the transfected cells were assayed for luceriferase and β-galactosidase activity. Each data point in this experiment represents the average of triplicate determinations of the transcriptional activity under given experimental conditions. The average coefficient of variation at each hormone concentrations was <10%. The data shown in FIG. 13A and 13B indicate that most of the known antiestrogens manifest agonist activity on mutated estrogen receptors. The fact that GW7604 does not exhibit agonist activity on any ER-mutant examined thus far indicates that this compound is useful in the treatment of tamoxifen refractory breast tumors.

Example 9

Figure 14A:
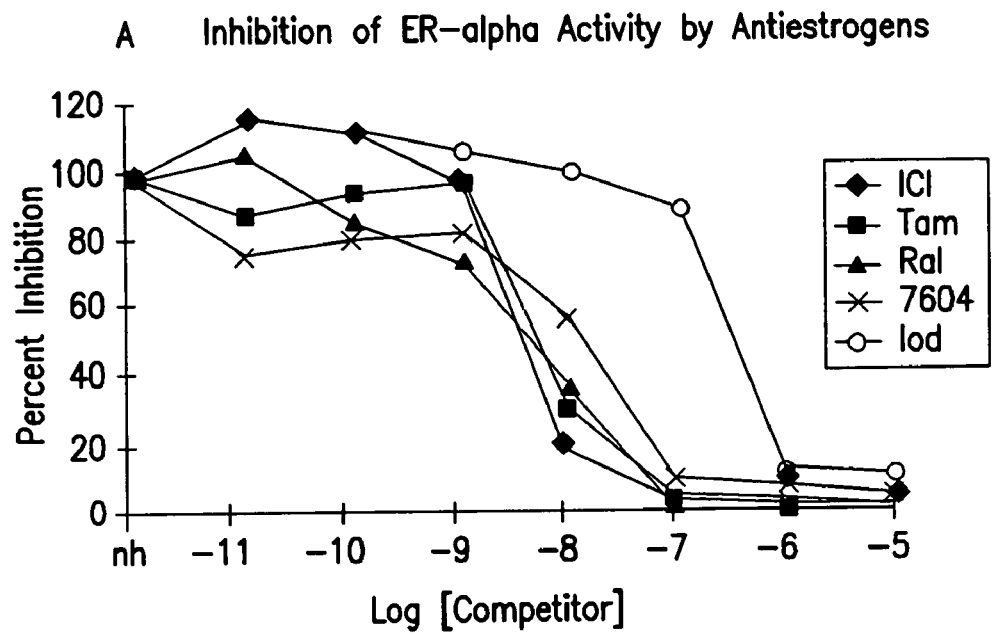
FIGS. 14A and 14B: A comparative analysis of the ability of a variety of antiestrogens to inhibit ERα (FIG. 14A) and ERβ (FIG. 14B) transcriptional activity.
Figure 14B:
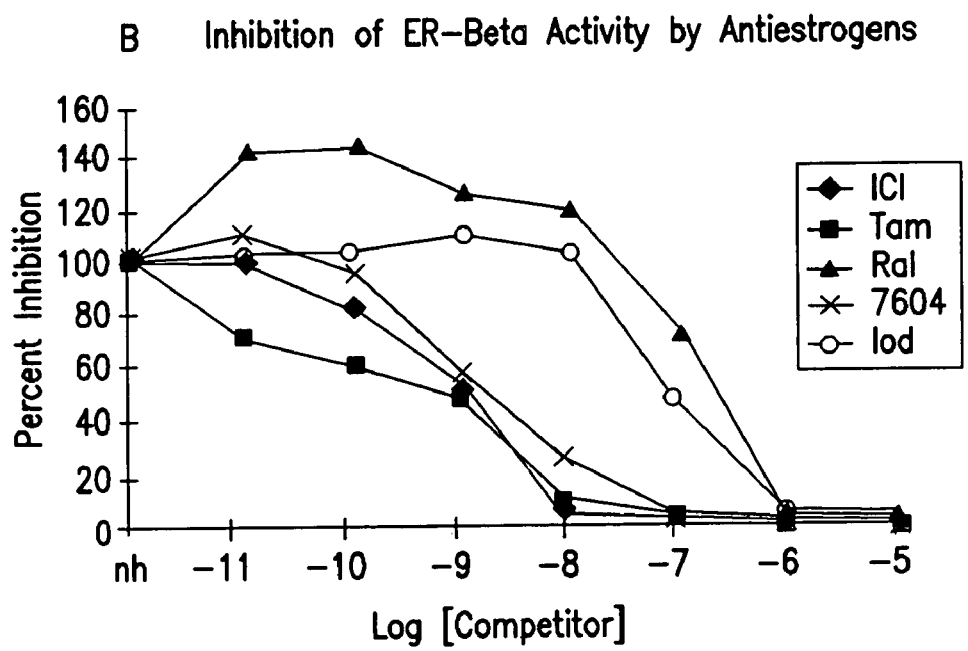

A Comparative Analysis of the Ability of a Variety of Antiestrogens to Inhibit ERα and ERβ Transcriptional Activity HeLa cells were transfected with either an ERα expression vector (see FIG. 14A) or an ERβ expression vector (see FIG. 14B) together with an estrogen responsive ERE-TK-luceriferase reporter construct. Subsequently, the ability of different concentrations of antagonist to inhibit estradiol ($10^{-9}$) activated transcription was assessed. The results shown in FIG. 14A and 14B indicate that with the exception of idoxifene, all antiestrogens manifest roughly equivalent activities on ERα, whereas on ERβ, neither raloxifene nor idoxifene manifest potent antagonist activity. Furthermore, these data indicate that GW7604 is a potent pan-antagonist of both forms of the human estrogen receptor.

Example 10

Figure 15A:
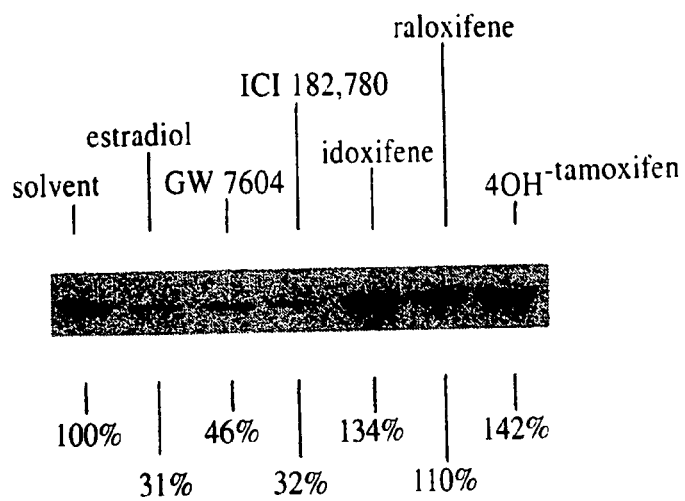
FIGS. 15A-15C: Western immunoblot analysis of ER expression in target cells following treatment with agonists or antagonists.
Figure 15B:
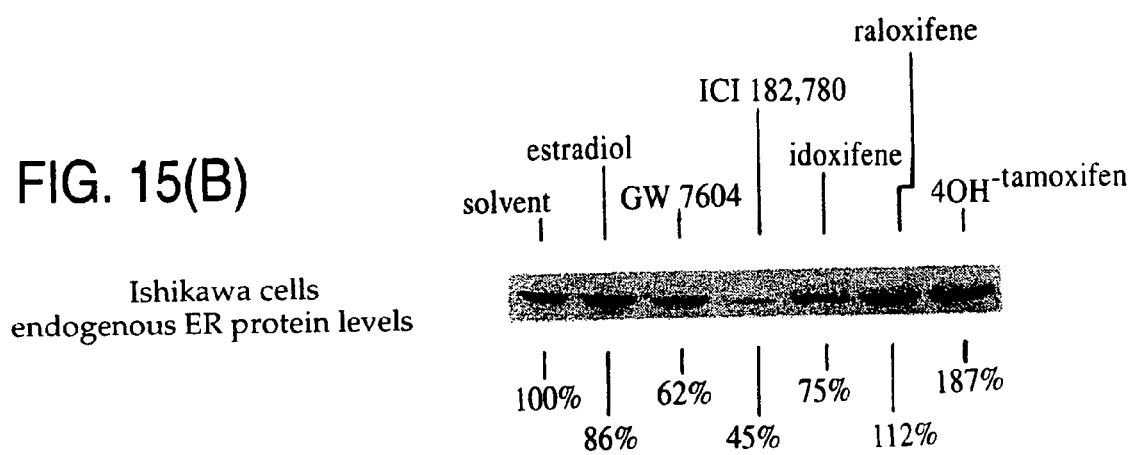
Figure 15C:
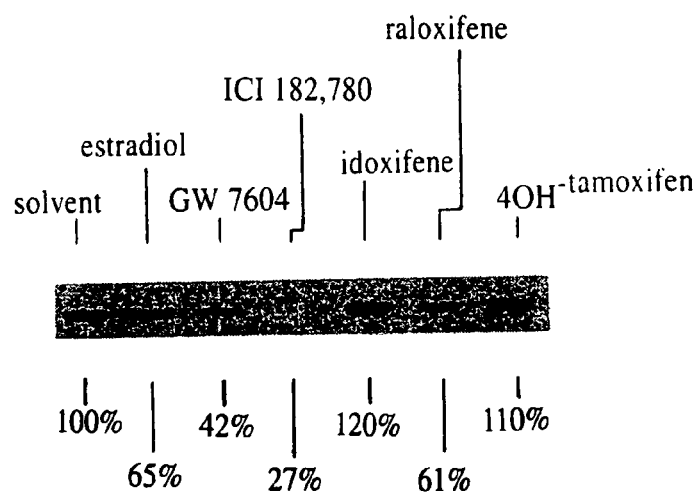

Western Immunoblot Analysis of ER Expression in Target Cells Following Treatment with Agonists or Antagonists The chosen cell lines were incubated for 48 h in the presence of solvent or 10 nM estradiol or antiestrogen as indicated. Nuclear extracts were prepared, and samples were separated by denaturing-PAGE, transferred to a nylon membrane, and the relative expression of ER following these treatments was estimated by western immunoblot using the ER-specific monoclonal antibody H222. FIG. 15A shows the endogenous nuclear ER content of MCF-7 cells (10 μg/lane). FIG. 15B shows the endogenous nuclear ER content of Ishikawa cells (100 μg/lane). FIG. 15C relates to Ishikawa cells transiently transfected with 0.9 μg/ml of ER (pRST7ER), 10 μg/lane of nuclear extract was used for detection. The ER levels was quantitated by densitometry of immunoblots. The results shown in FIG. 15A-15C are representative of multiple experiments performed under the same conditions.

Example 11

Figure 16A:
FIGS. 16A and 16B: Western immunoblot analysis of endogenous ER expression in MCF-7 cells following short term treatments (FIG. 16A. 1 h and FIG. 16B. 4 h) with agonists or antagonists.
Figure 16B:
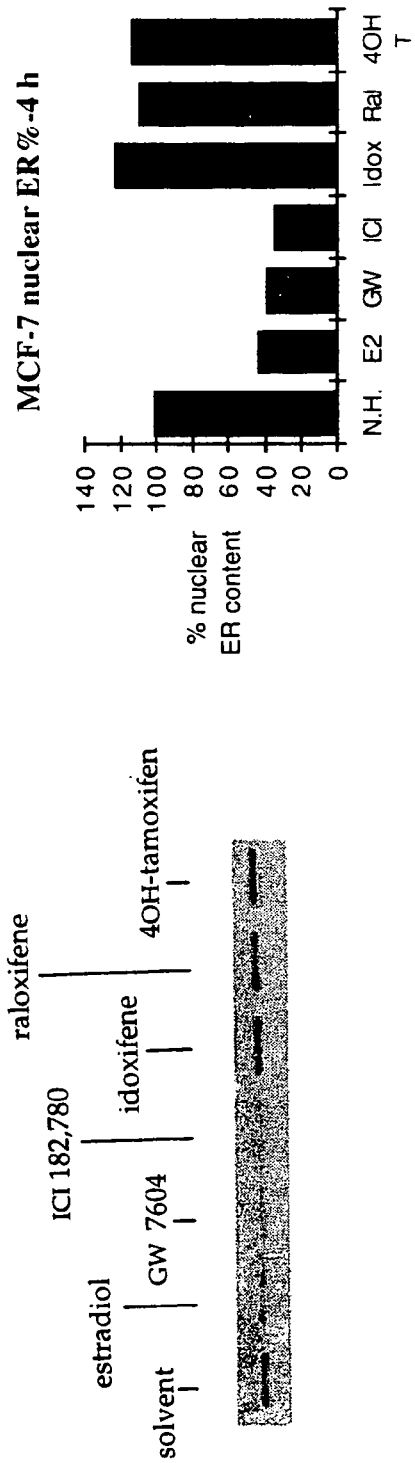

Western Immunoblot Analysis of Endogenous ER Expression in MCF-7 Cells Following Short Term Treatments with Agonists or Antagonists Human breast cancer MCF-7 cells were induced for 1 h (FIG. 16A) or 4 h (FIG. 16B) in the presence of solvent or 10 nM estradiol or antiestrogen as indicated. Nuclear extracts were prepared, and samples were separated by denaturing-PAGE, transferred to a nylon membrane, and the relative expression of ER following these treatments was estimated by western immunoblot using the ER-specific monoclonal antibody H222. The ER levels were quantitated by densitometry of immunoblots. The results shown in FIG. 16A and 16B are representative of multiple experiments performed under the same conditions.

Example 12

Figure 17A:
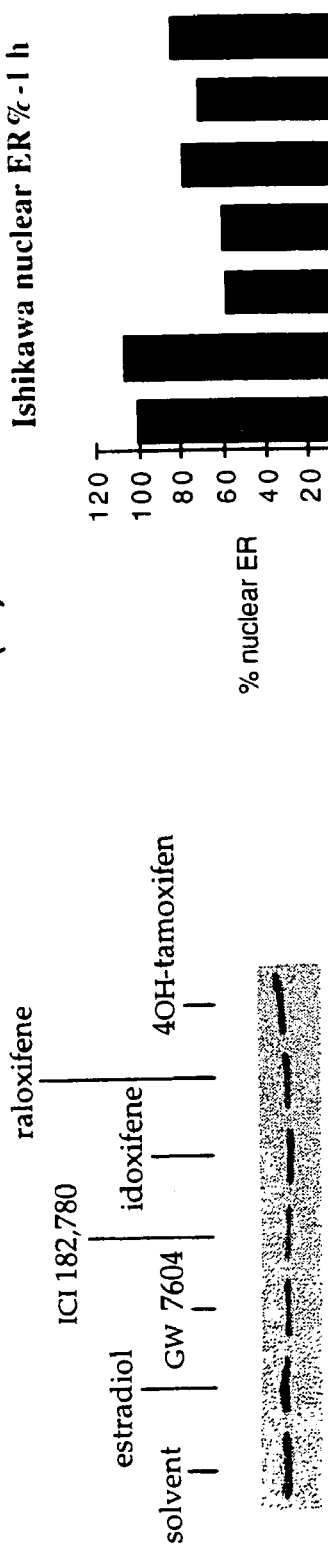
FIGS. 17A and 17B: Western immunoblot analysis of endogenous ER expression in Ishikawa cells following short term treatments (FIG. 17A. 1 h and FIG. 17B. 4 h) with agonists or antagonists.
Figure 17B:
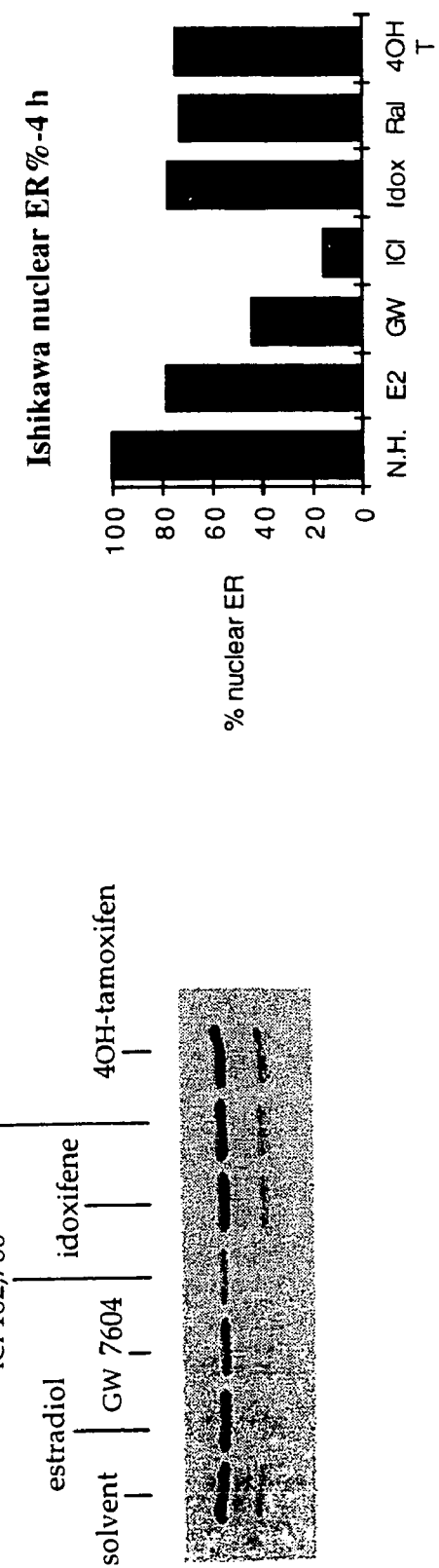

Western Immunoblot Analysis of Endogenous ER Expression in Ishikawa Cells (Cultured Uterine Cells) Following Short Term Treatments with Agonists or Antagonists Human endometrial adenocarcinoma Ishiwaka cells were incubated for 1 h (FIG. 17A) or 4 h (FIG. 17B) in the presence of solvent or 10 nM estradiol or antiestrogen as indicated. Nuclear extracts were prepared, and samples were separated by denaturing-PAGE, transferred to a nylon membrane, and the relative expression of ER following these treatments was estimated by western immunoblot using the ER-specific monoclonal antibody H222. The ER levels were quantitated by densitometry of immunoblots. The results shown in FIG. 17A and 17B are representative of multiple experiments performed under the same conditions.

Example 13

Figure 18A:
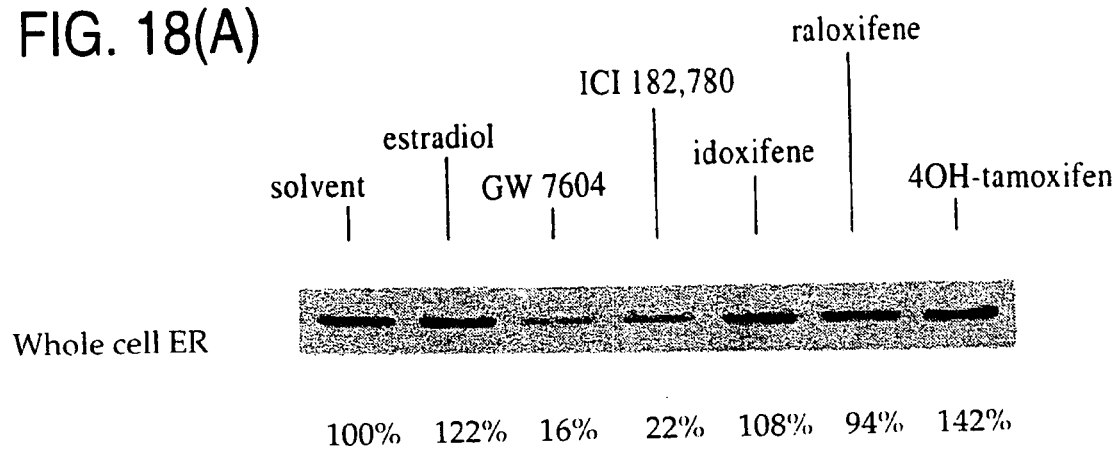
FIGS. 18A-18C: Western immunoblot analysis of whole cell (FIG. 18A), nuclear (FIG. 18B) and cytoplasmic (FIG. 18C) endogenous ER expression in Ishikawa cells following short term treatments with agonists or antagonists.
Figure 18B:
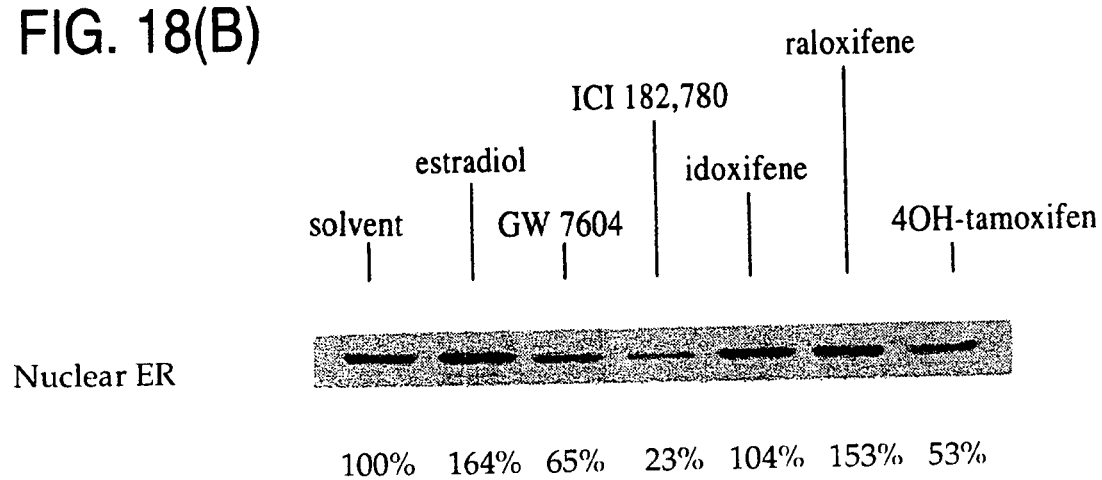
Figure 18C:
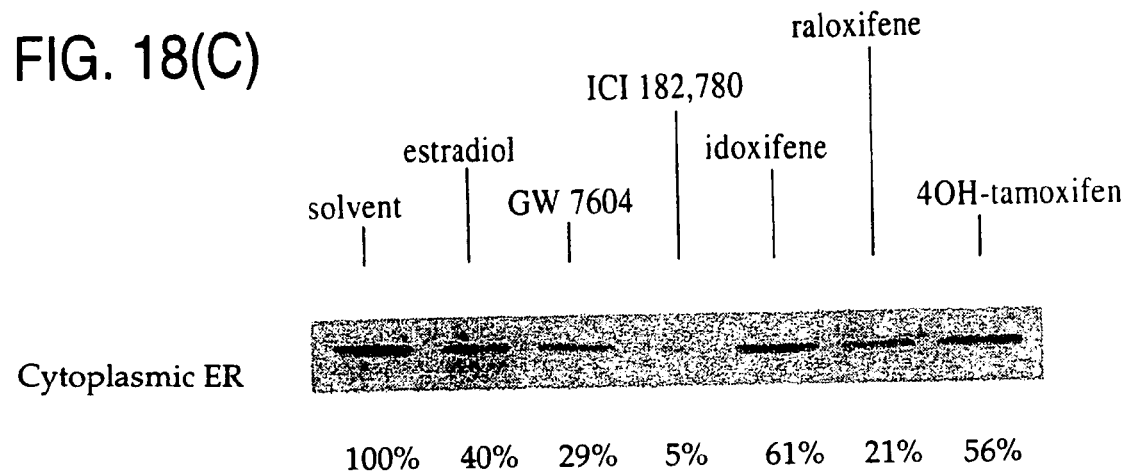

Western Immunoblot Analysis of Whole Cell, Nuclear and Cytoplasmic Endogenous ER Expression in Ishikawa Cells Following Short-Term Treatments with Agonists or Antagonists Human endometrial adenocarcinoma Ishikawa cells were induced for 1 h in the presence of solvent or 10 nM estradiol or antiestrogen. Whole cell (FIG. 18A), nuclear (FIG. 18B) and cytoplasmic (FIG. 18C) extracts were prepared, and samples were separated by denaturing-PAGE, transferred to a nylon membrane, and the relative expression of ER following the treatment was estimated by Western immunoblot using the ER-specific monoclonal antibody H222. The ER levels was quantitated by densitometry of immunoblots. The results shown in FIG. 18A-18C are representative of multiple experiments performed under the same conditions.

Example 14

GW7604 Inhibits E2 Stimulated MCF-7 Cell Proliferation

Goal: Determine the ability of GW5638 to inhibit estrogen-stimulated cell proliferation of MCF-7 breast cancer in vivo.

Experimental Design: Plate between 25,000 and 50,000 cells per well onto 24-well plates. Cells are plated in phenol red-free media. After attachment, cells are stimulated with either antiestrogen alone or estrogen and antiestrogen. Induction time ranges from 12-48 hours, depending on experiment.

Add 4λ (4 μCi) thymidine, [methyl-$^3$H]-to each well.
Incubate at 37° C. for 2-4 hours.
Aspirate media and wash twice with ice cold PBS.
Wash once with ice cold 10% TCA (trichloroacetic acid).
Add 2 mL 10% TCA to each well.
Incubate at 4° C. for 1-2 hours.

Wash once with TCA.

Add 1 mL 0.2N NaOH.

Transfer each well to scintillation vial containing 2 mL scintillation fluid.

Vortex and count [$^3$H].

Figure 19A:
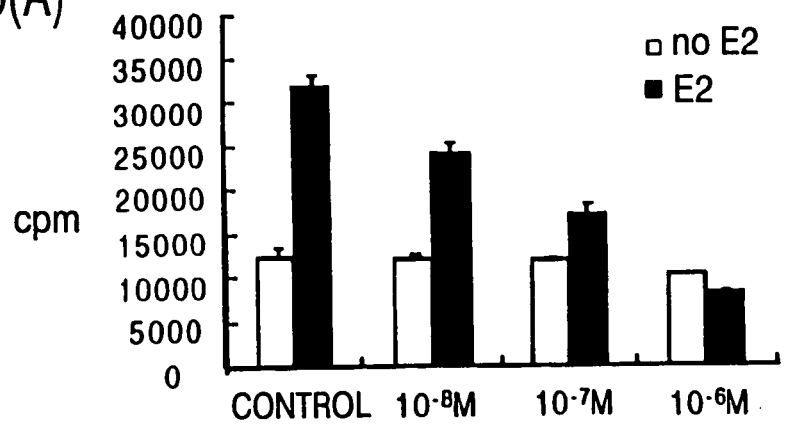
FIGS. 19A-19C: Effect on E2 stimulated MCF-7 cell proliferation.
Figure 19B:
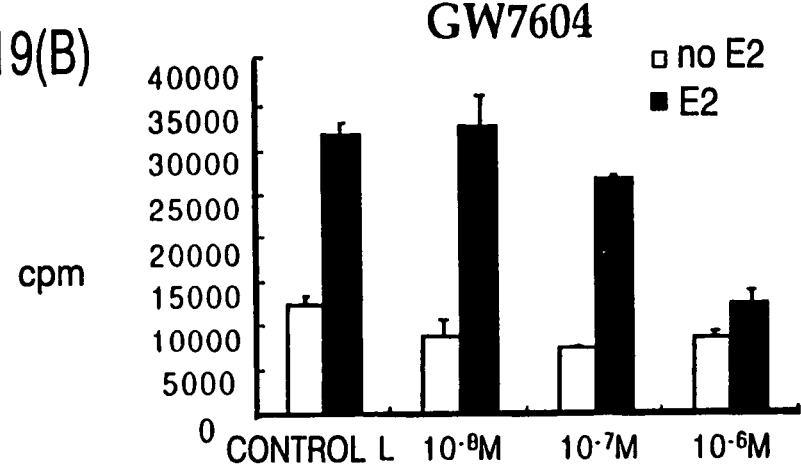
Figure 19C:
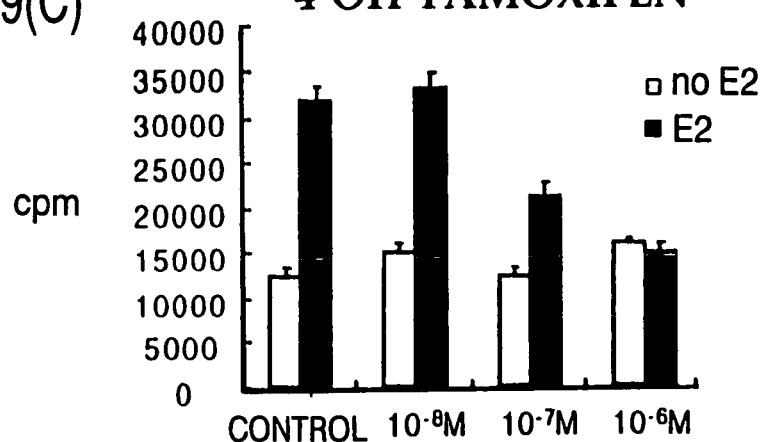

Results will indicate the ability of the various compounds to inhibit estrogen-induced and basal cell proliferation of MCF-7 cells. (See FIG. 19A-19C.)

All documents cited above are hereby incorporated in their entirety by reference.

One skilled in the art will appreciate from a reading of this disclosure that various changes in form and detail can be made without departing from the true scope of the invention.

TABLE 1

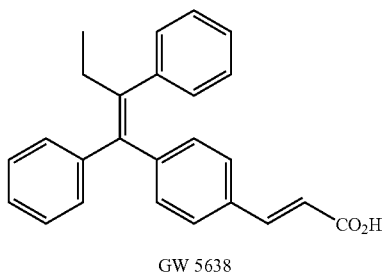

GW 5638

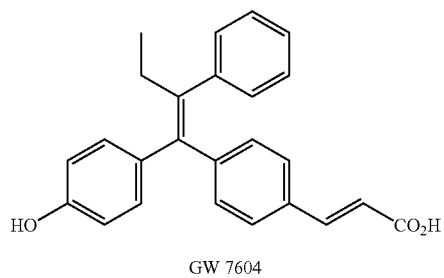

GW 7604

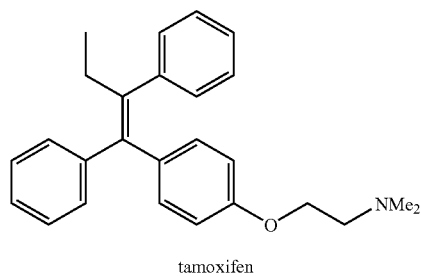

tamoxifen

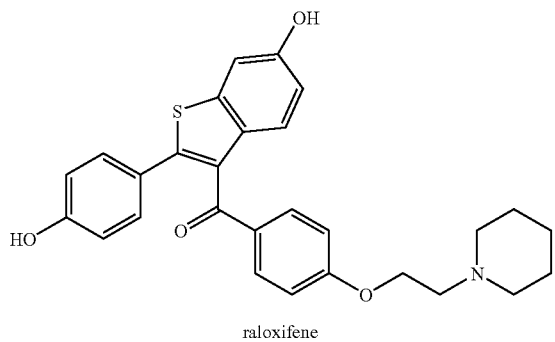

raloxifene

TABLE 1-continued

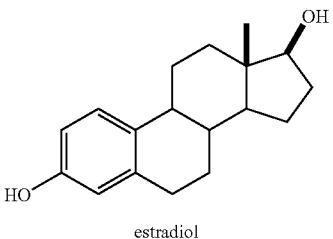

estradiol

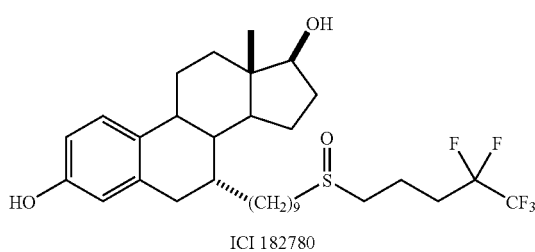

ICI 182780

What is claimed is:

1. A method of treating an estrogen-stimulated cancer in a mammal comprising administering to said mammal an amount of a compound of Formula I:

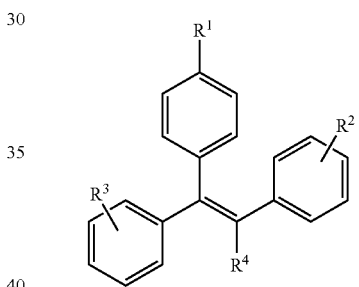

wherein $R^1$ is —$(CH_2)_n CR^5$=$CR^6 R^7$

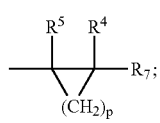

$R^2$ and $R^3$ are independently H, —$CH_3$, —OH, —$OCH_3$, —$OCH_2CH_3$ or —$CH(CH_3)_2$;

$R^4$ is —CN, —$NO_2$, —$CH_3$, —$CH_2CH_3$, —$CH_2CH_2$—Y or —Y;

$R^5$ and $R^6$ are independently H, —$C_{1-4}$alkyl, —$C_{2-4}$alkenyl, —$C_{2-4}$alkynyl, —X—$C_{1-3}$alkyl, —X—$C_{2-4}$alkenyl, —X—$C_{2-4}$alkynyl or —Y;

$R^7$ is —$C(O)OR^{12}$ $R^{12}$ is H;

X is oxygen or sulfur;

Y is a halogen; and n is an integer selected from 0, 1 or 2;

or pharmaceutically acceptable salt thereof, sufficient to effect said treatment, said cancer being resistant to an estrogen receptor modulator other than said compound of Formula I.

2. The method according to claim 1 wherein said cancer is breast cancer, uterine cancer, ovarian cancer or colon cancer.

3. The method according to claim 2 wherein said cancer is breast cancer.

4. The method according to claim 1 wherein said cancer is resistant to tamoxifen, idoxifene, raloxifene or ICI 182,780.

5. The method according to claim 1 wherein said cancer is de novo resistant to said estrogen receptor modulator.

6. The method according to claim 1 wherein said resistance to said estrogen receptor modulator is acquired.

7. The method according to claim 1 wherein said compound is GW5638 or GW7604.

8. The method according to claim 1 further comprising administering to said mammal an effective an amount of at least one compound selected from the group consisting of an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

* * * * *